(12) United States Patent
Villamar

(10) Patent No.: US 10,194,601 B2
(45) Date of Patent: Feb. 5, 2019

(54) SYSTEM AND METHOD FOR SOLAR GREENHOUSE AQUAPONICS AND BLACK SOLDIER FLY COMPOSTER AND AUTO FISH FEEDER

(71) Applicant: Carlos R. Villamar, Falls Church, VA (US)

(72) Inventor: Carlos R. Villamar, Falls Church, VA (US)

(*) Notice: Subject to any disclaimer, the term of this patent is extended or adjusted under 35 U.S.C. 154(b) by 0 days.

(21) Appl. No.: 15/917,839

(22) Filed: Mar. 11, 2018

(65) Prior Publication Data

US 2018/0249649 A1    Sep. 6, 2018

Related U.S. Application Data

(60) Continuation-in-part of application No. 15/783,684, filed on Oct. 13, 2017, now Pat. No. 10,015,940,
(Continued)

(51) Int. Cl.
*A01G 31/02* (2006.01)
*G01N 21/27* (2006.01)
(Continued)

(52) U.S. Cl.
CPC ............. *A01G 31/02* (2013.01); *A01G 9/14* (2013.01); *A01K 61/10* (2017.01); *A01K 61/80* (2017.01);
(Continued)

(58) Field of Classification Search
CPC ...... A01G 9/14; A01G 9/1415; A01G 9/1484; A01G 9/24; A01G 9/247; A01G 31/00; A01G 31/02
(Continued)

(56) References Cited

U.S. PATENT DOCUMENTS

| | | | | |
|---|---|---|---|---|
| 5,046,451 A * | 9/1991 | Inslee | | A01G 31/02 119/227 |
| 5,335,447 A * | 8/1994 | Bee | | A01G 9/225 47/17 |
| 6,131,363 A * | 10/2000 | Phillips | | A01G 9/1438 52/786.11 |
| 8,915,015 B1 * | 12/2014 | Augspurger | | A01G 9/14 47/17 |

(Continued)

OTHER PUBLICATIONS

NVAC Greenhouse (Natural Ventilation Augmented Cooling), "McGill researchers develop new passive cooling and ventilation solution," Horti Daily, publication date Feb. 2, 2017, availableon World Wide Web at http://www.hortidaily.com/article/32005/McGill-researchers-develop-new-passive-cooling-and-ventilation-solution.
(Continued)

*Primary Examiner* — Monica L Williams
*Assistant Examiner* — Aaron M Rodziwicz
(74) *Attorney, Agent, or Firm* — Carlos R. Villamar; The Villamar Firm PLLC

(57) ABSTRACT

An aquaponics and greenhouse system, includes a solar greenhouse insulated on north, east and west sides and with glazing on a south side at an angle to maximize winter sunlight, and housing a fish tank, grow beds, and a hard filter. The grow beds and hard filter include geyser pumps in the fish tank powered by air pumps that pump water from the fish tank to the grow bed or hard filter and aerate fish tank water. The hard filter includes algae layer with an air stone powered by an air pump underneath to aerate the algae. Grow beds on the north side have a barrier layer over media, and with a mushroom bulk substrate layer disposed thereover. The air intake of the air pump of the hard filter or the air stone extract $CO_2$ from the mushroom bulk substrate and pump the extracted $CO_2$ to the algae layer.

8 Claims, 14 Drawing Sheets

Related U.S. Application Data which is a division of application No. 15/446,863, filed on Mar. 1, 2017, now Pat. No. 9,788,496, which is a continuation-in-part of application No. 14/633,387, filed on Feb. 27, 2015, now Pat. No. 9,585,315.

(60) Provisional application No. 61/946,690, filed on Feb. 28, 2014.

(51) Int. Cl.
| | | |
|---|---|---|
| *A01K 67/033* | (2006.01) | |
| *A01K 63/06* | (2006.01) | |
| *A01K 63/04* | (2006.01) | |
| *A01K 61/80* | (2017.01) | |
| *A01K 61/10* | (2017.01) | |
| *A01G 9/14* | (2006.01) | |
| *G01N 33/18* | (2006.01) | |
| *G01N 33/00* | (2006.01) | |

(52) U.S. Cl.
CPC .......... *A01K 63/042* (2013.01); *A01K 63/045* (2013.01); *A01K 63/047* (2013.01); *A01K 63/065* (2013.01); *A01K 67/033* (2013.01); *G01N 21/27* (2013.01); *G01N 33/004* (2013.01); *G01N 33/1886* (2013.01); *G01N 2201/12* (2013.01)

(58) Field of Classification Search
USPC .............................. 47/1.4, 17, 62 R; 119/226
See application file for complete search history.

(56) References Cited

U.S. PATENT DOCUMENTS

| | | | | |
|---|---|---|---|---|
| 2003/0024874 A1* | 2/2003 | Wallace | ............ | C02F 3/00 210/602 |
| 2007/0062105 A1* | 3/2007 | Stevens | ............ | A01G 9/14 47/17 |
| 2007/0166171 A1* | 7/2007 | Kondo | ............ | F04F 1/18 417/118 |
| 2009/0301399 A1* | 12/2009 | Brown | ............ | A01G 31/02 119/226 |
| 2010/0031893 A1* | 2/2010 | Bodlovich | ............ | C02F 3/32 119/227 |
| 2010/0038440 A1* | 2/2010 | Ersavas | ............ | A01G 25/167 236/51 |
| 2011/0167716 A1* | 7/2011 | Myntti | ............ | A01G 9/243 47/17 |
| 2012/0067339 A1* | 3/2012 | Hall | ............ | F24S 23/80 126/621 |
| 2012/0174478 A1* | 7/2012 | Chen | ............ | A01G 9/243 47/17 |
| 2013/0008386 A1* | 1/2013 | Jacobs | ............ | A01K 63/02 119/217 |
| 2015/0196880 A1 | 7/2015 | Stone et al. | | |
| 2015/0223407 A1* | 8/2015 | Carroll | ............ | A01G 9/243 47/17 |

OTHER PUBLICATIONS

MMariola. (Jun. 29, 2012). Sustainability@Wooster. Retrieved from Sustainability.com: http://sustainability.scotblogs.wooster.edu/page/4/.

* cited by examiner

FIG. 1 TOP VIEW 100

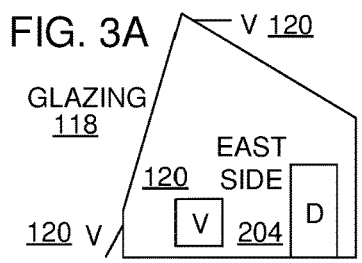
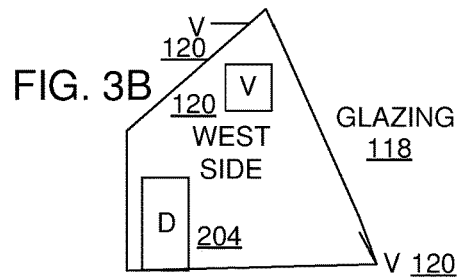
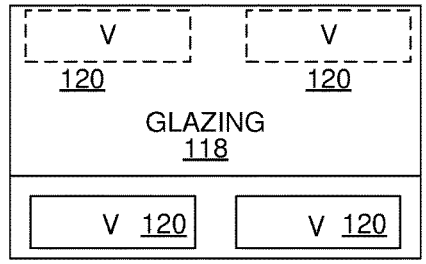
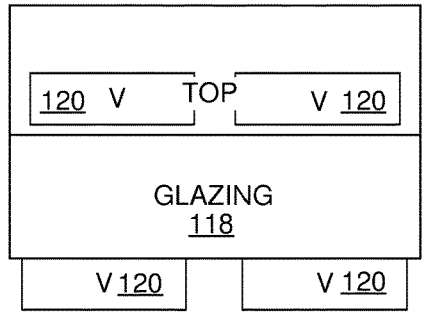
VENT/DOOR LAYOUTS 300
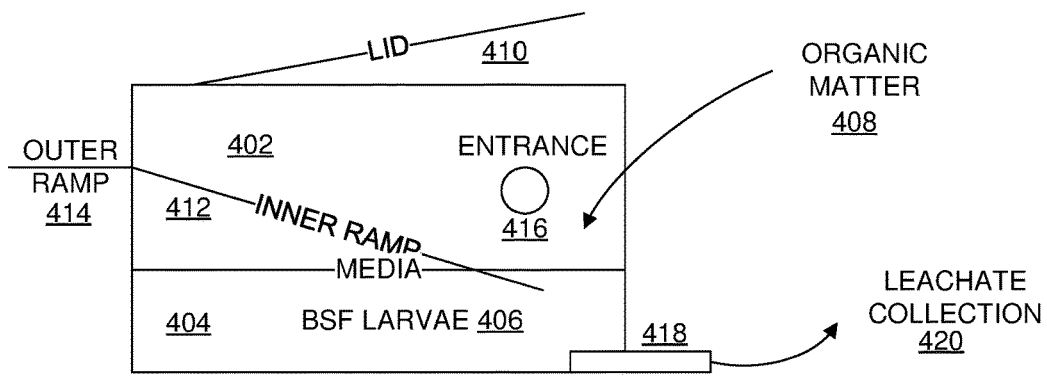
FIG. 4  BSF AUTO FISH FEEDER (BSF) 122
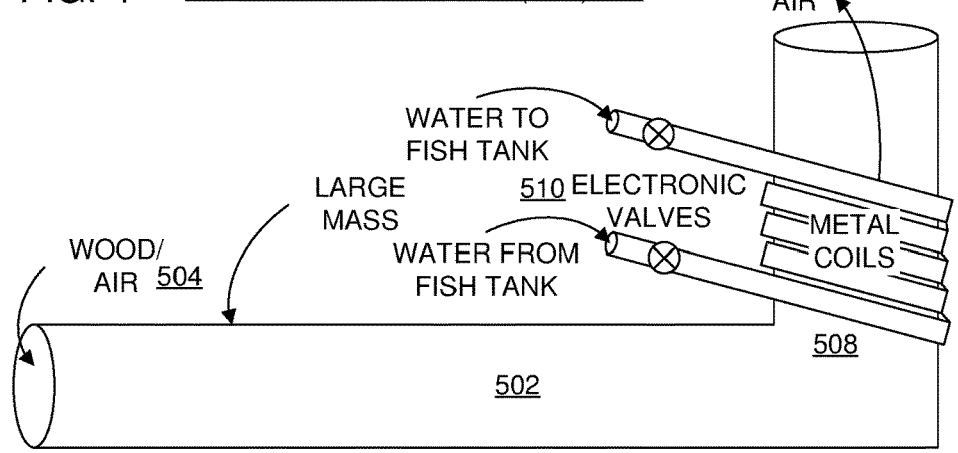
FIG. 5  ROCKET MASS HEATER (RMH) 104

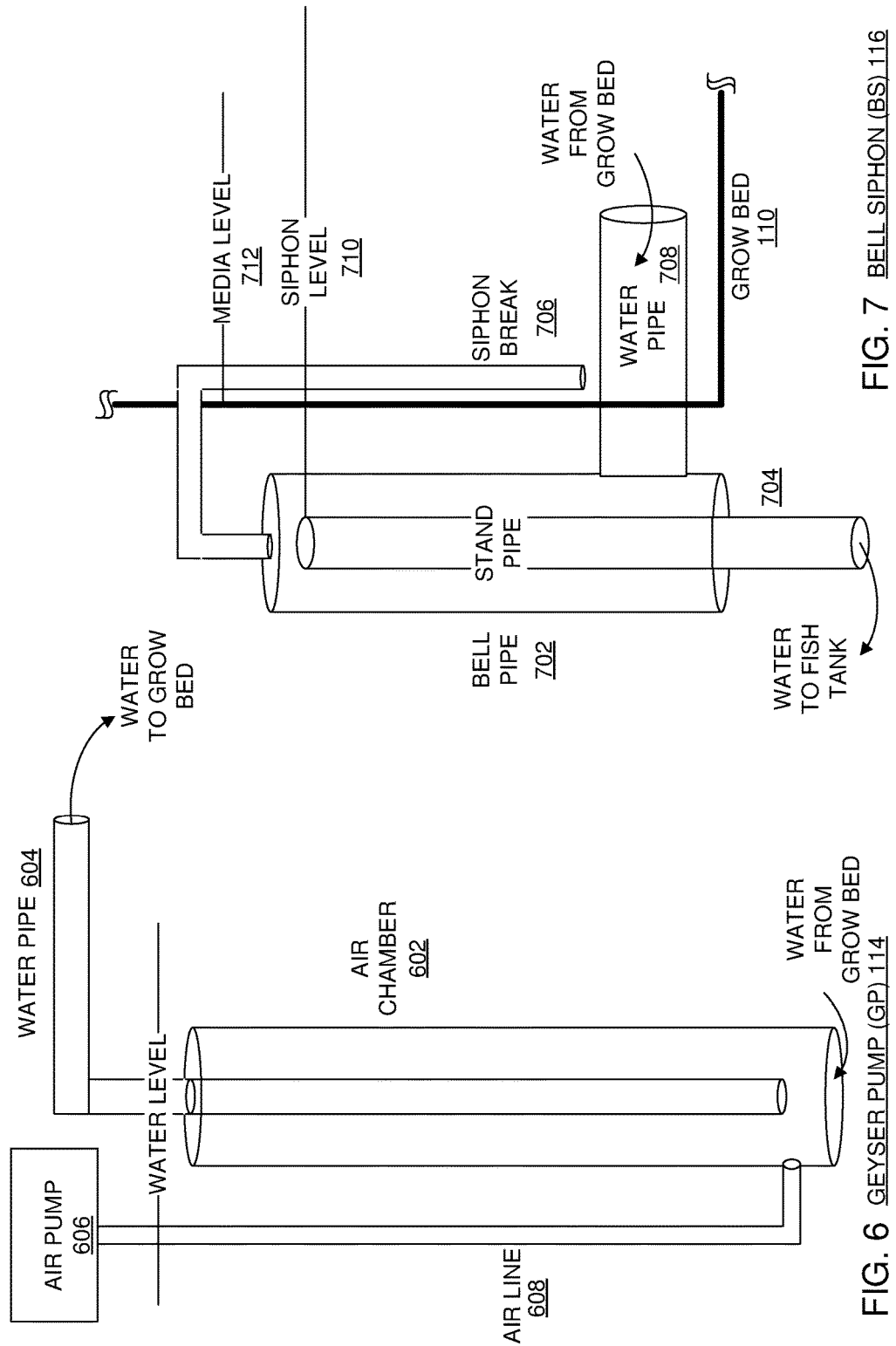
FIG. 7 BELL SIPHON (BS) 116
FIG. 6 GEYSER PUMP (GP) 114

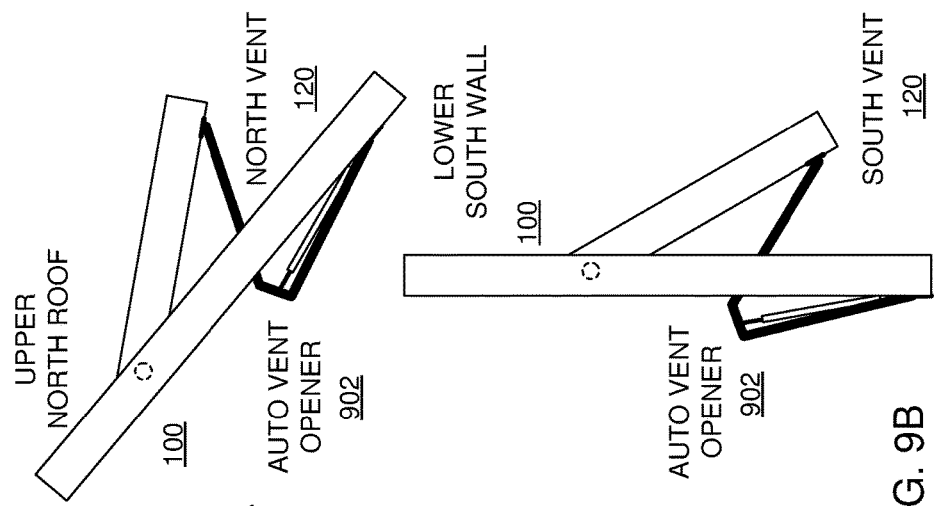
FIG. 9A
FIG. 9B AUTO VENT OPENER 900
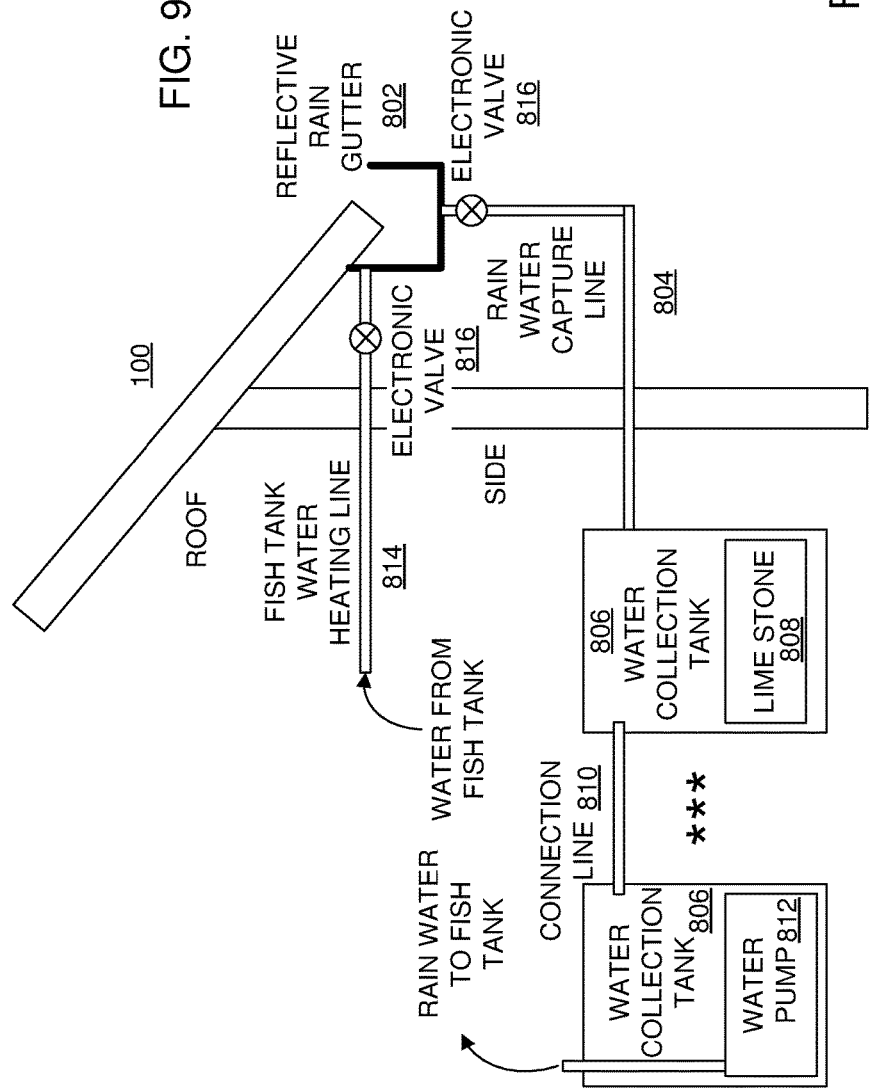
FIG. 8 RAIN WATER COLLECTION (RWC) 106

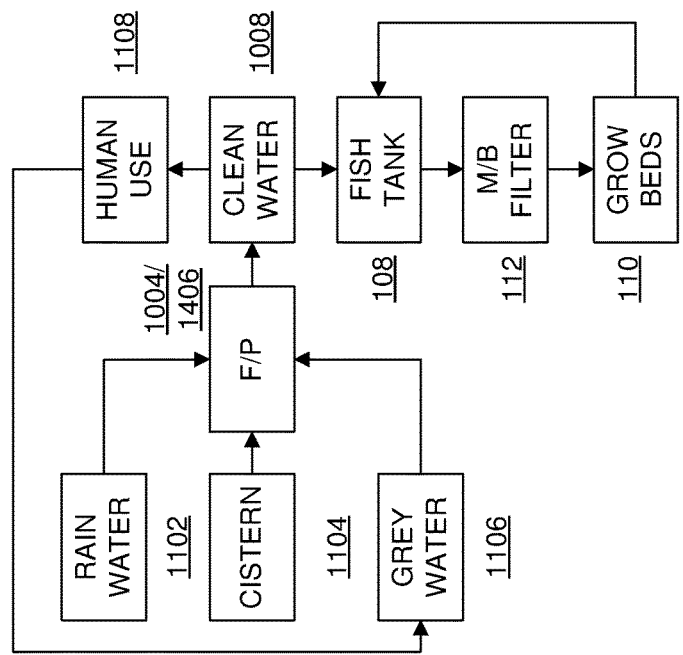
FIG. 11    WATER LOOP 1100
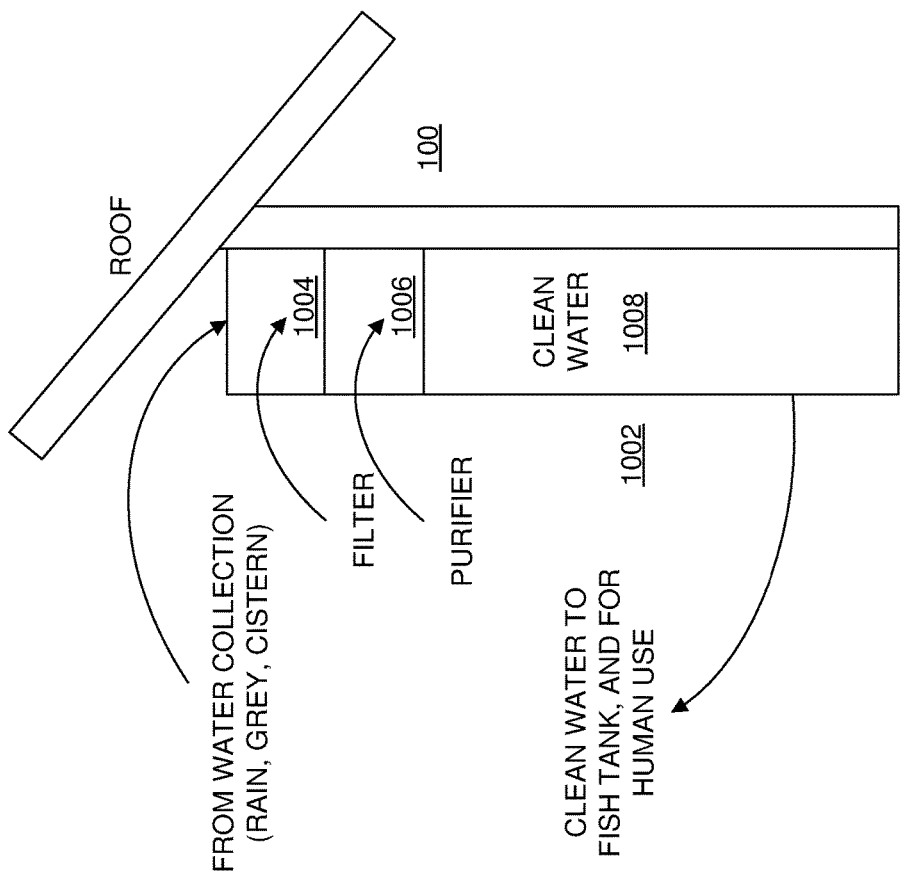
FIG. 10    WATER WALL 1000

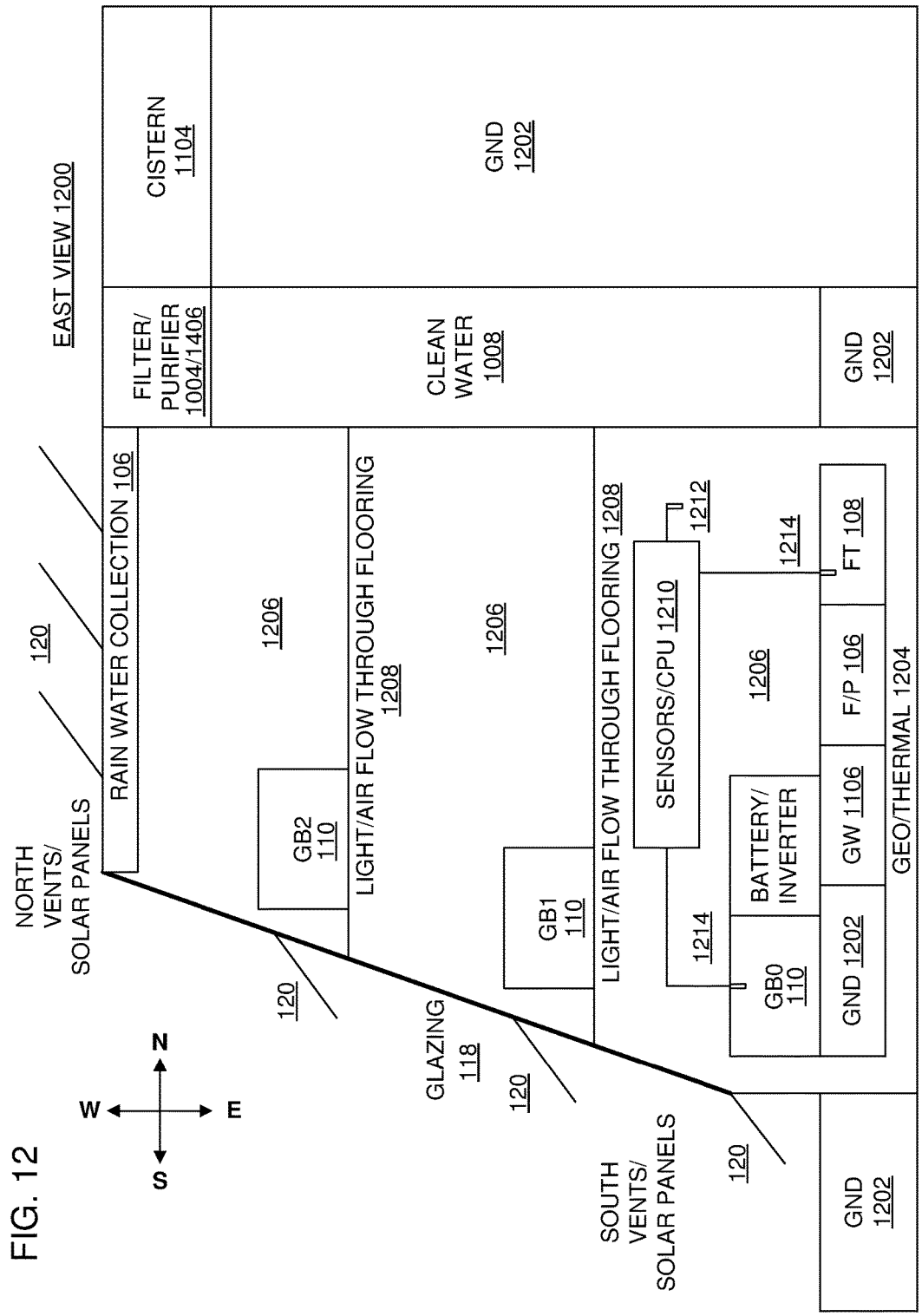

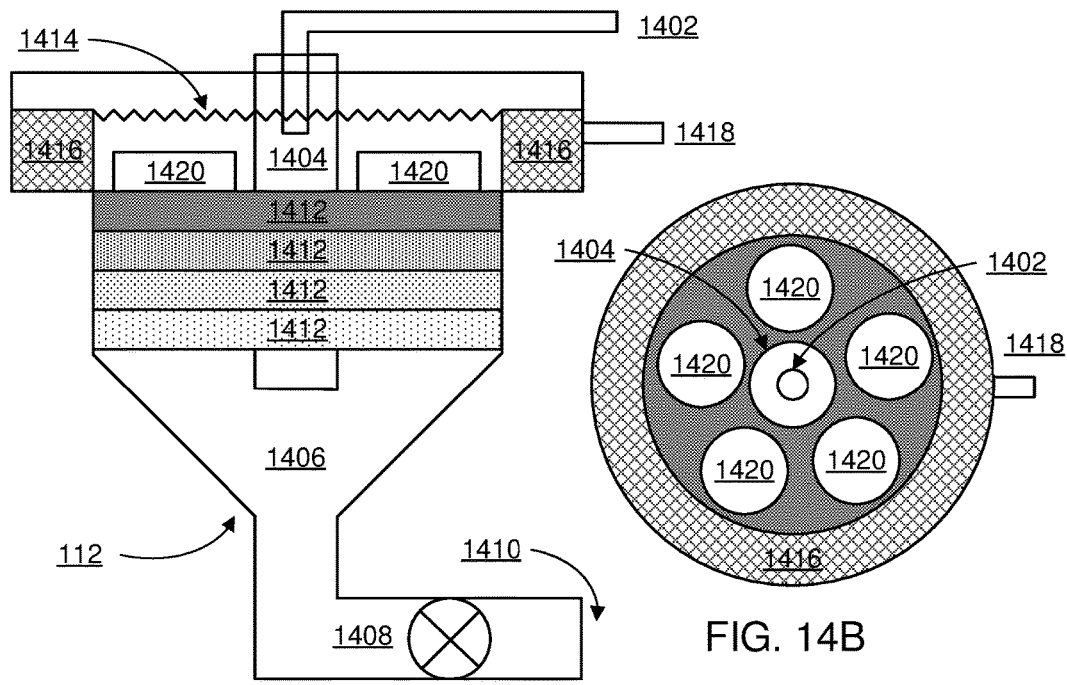
FIG. 14A    HARD FILTER (HF) 112
FIG. 14B
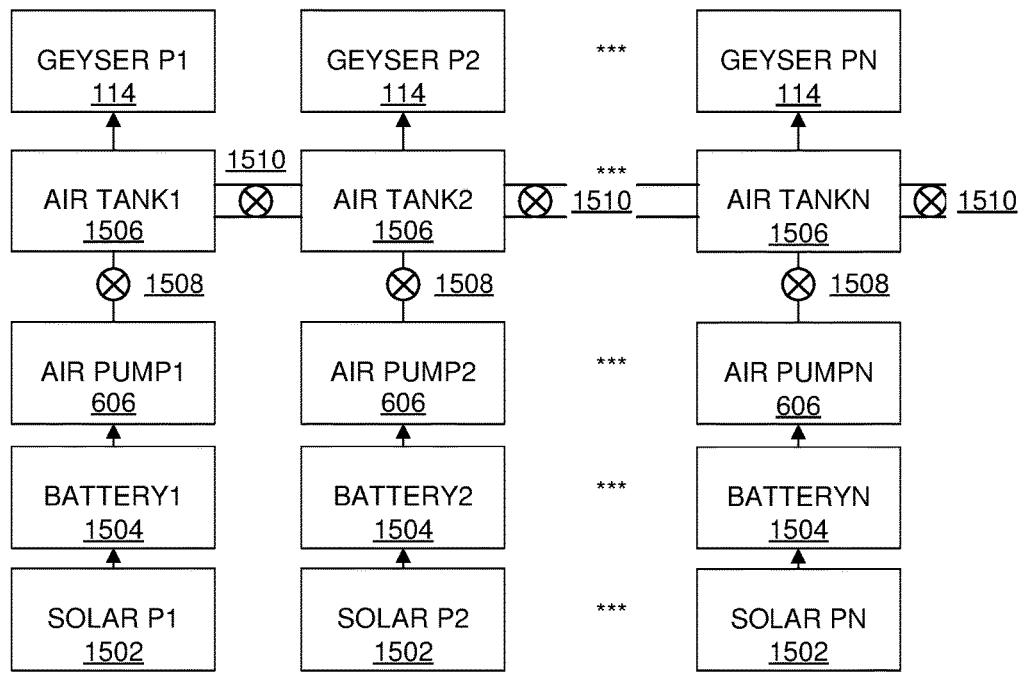
FIG. 15    GEYSER PUMP (GP) 114

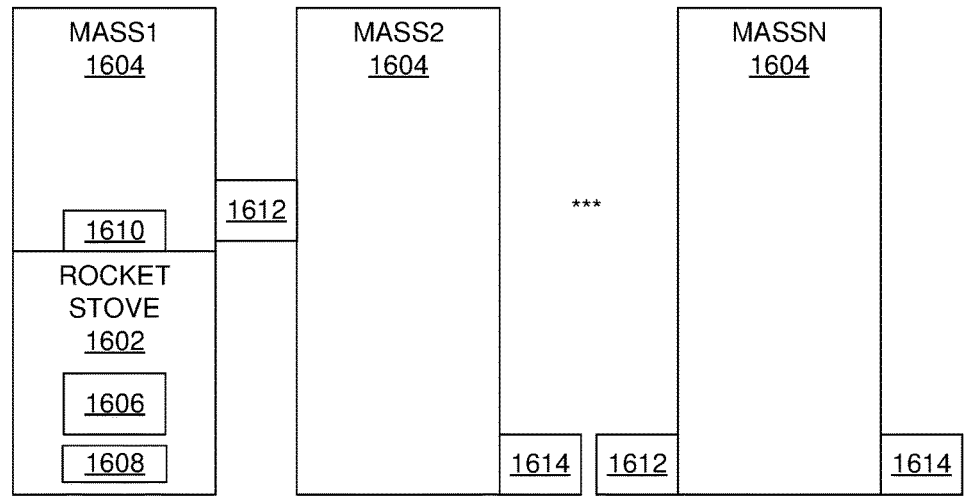
FIG. 16    ROCKET MASS HEATER (RMH) 104
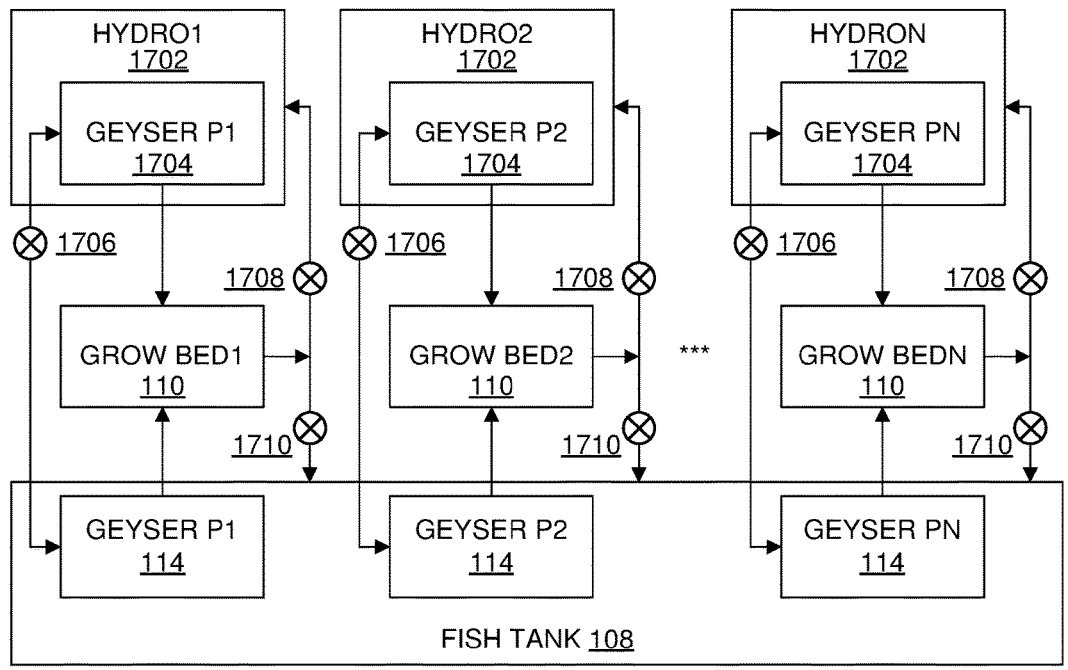
FIG. 17    AQUAPONICS/HYDRO ON DEMAND 1700

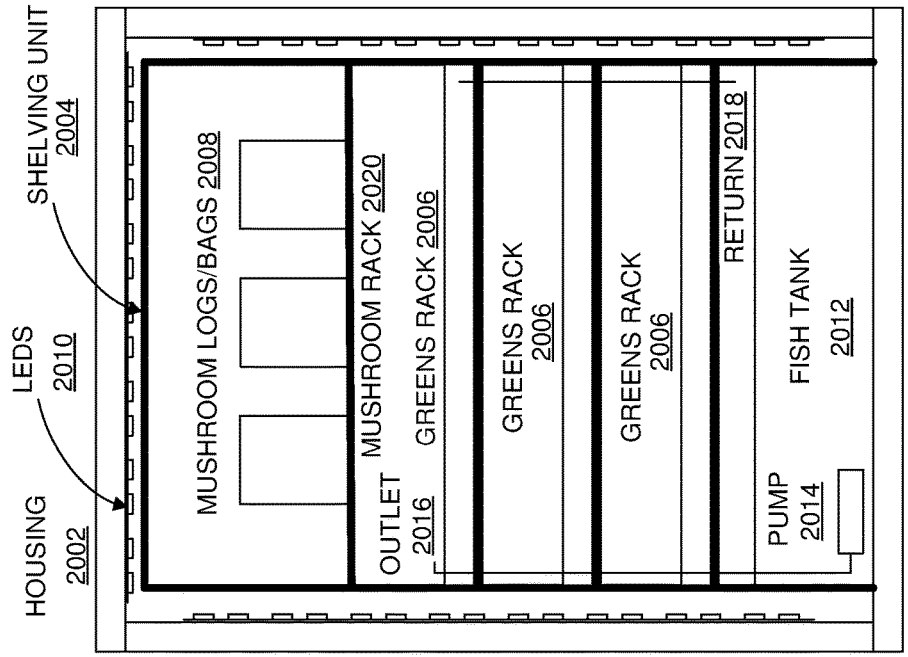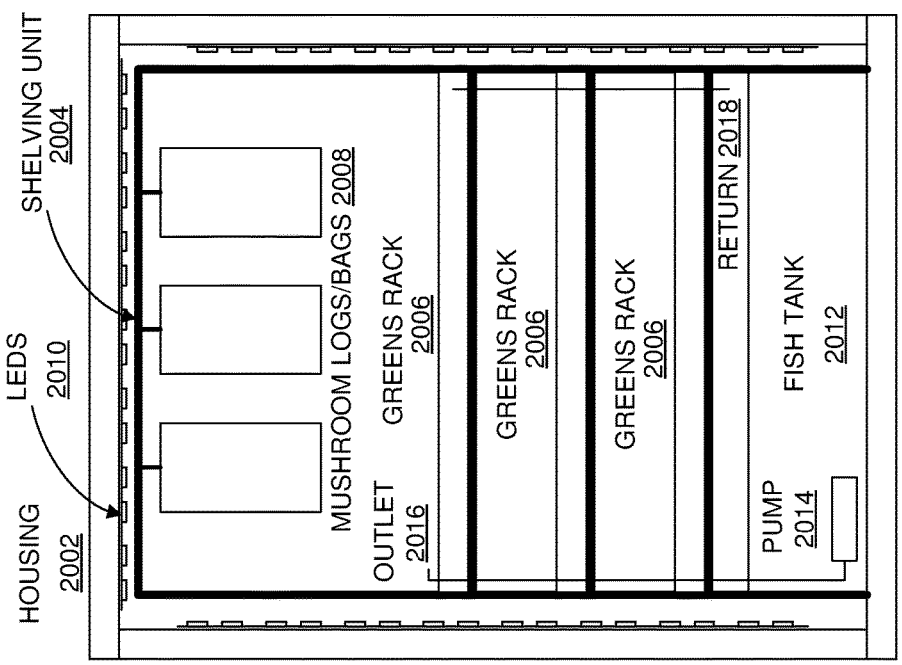

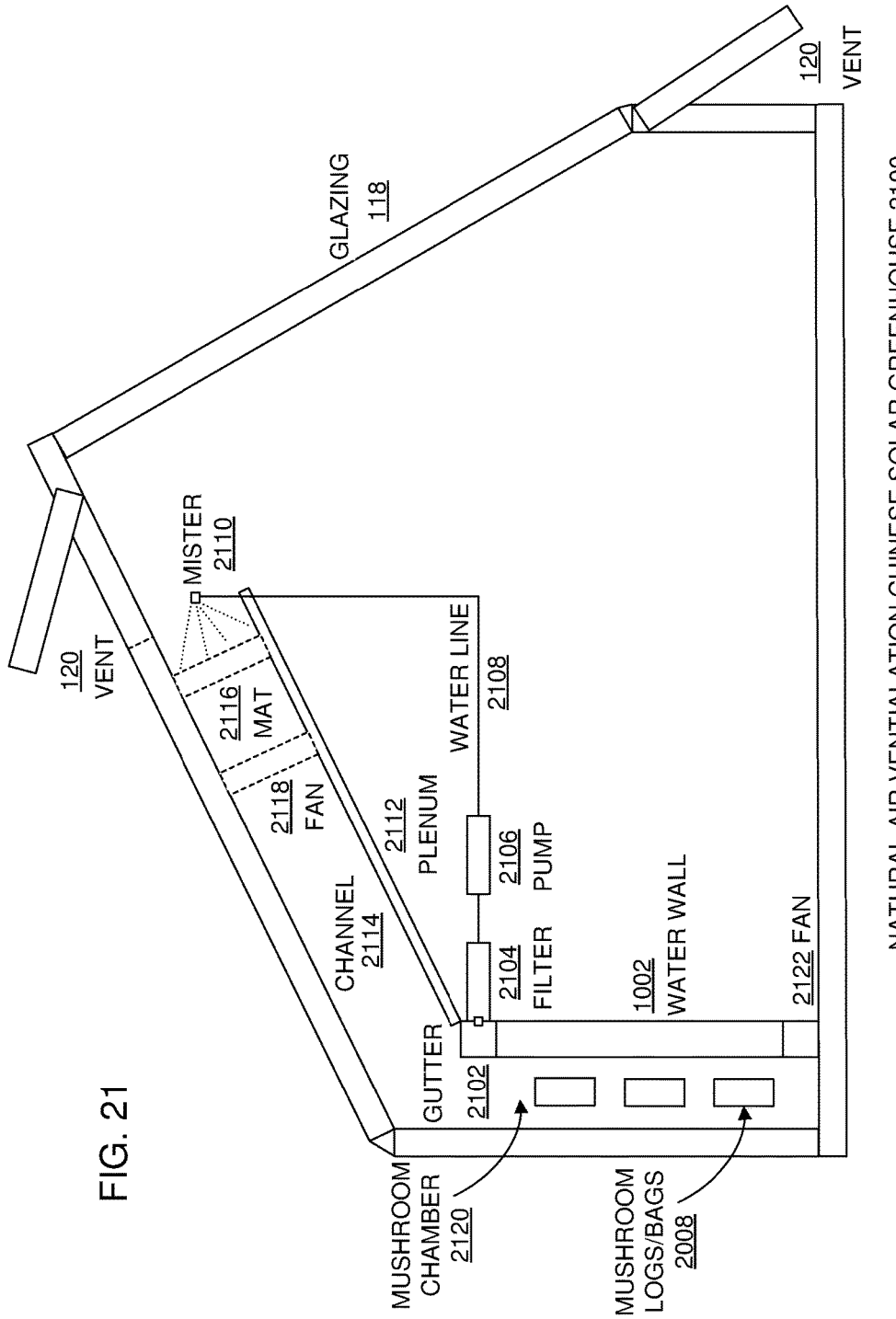

SYSTEM AND METHOD FOR SOLAR GREENHOUSE AQUAPONICS AND BLACK SOLDIER FLY COMPOSTER AND AUTO FISH FEEDER

CROSS REFERENCE TO RELATED DOCUMENTS

The present invention is a continuation-in-part of U.S. patent application Ser. No. 15/783,684 of Carlos R. VILLAMAR, entitled "SYSTEM AND METHOD FOR SOLAR GREENHOUSE AQUAPONICS AND BLACK SOLDIER FLY COMPOSTER AND AUTO FISH FEEDER," filed on 13 Oct. 2017, now pending, which is a divisional of U.S. patent application Ser. No. 15/446,863 of Carlos R. VILLAMAR, entitled "SYSTEM AND METHOD FOR SOLAR GREENHOUSE AQUAPONICS AND BLACK SOLDIER FLY COMPOSTER AND AUTO FISH FEEDER," filed on 1 Mar. 2017, now U.S. Pat. No. 9,788,496, which is a continuation-in-part of U.S. patent application Ser. No. 14/633,387 of Carlos R. VILLAMAR, entitled "SYSTEM AND METHOD FOR SOLAR GREENHOUSE AQUAPONICS AND BLACK SOLDIER FLY COMPOSTER AND AUTO FISH FEEDER," filed on 27 Feb. 2015, now U.S. Pat. No. 9,585,315, which claims priority to U.S. Provisional Patent Application Ser. No. 61/946,690 of Carlos R. VILLAMAR, entitled "SYSTEM AND METHOD FOR SOLAR GREENHOUSE AQUAPONICS AND BLACK SOLDIER FLY COMPOSTER AND AUTO FISH FEEDER," filed on 28 Feb. 2014, the entire disclosures of all of which are hereby incorporated by reference herein.

BACKGROUND OF THE INVENTION

Field of the Invention

The present invention generally relates to systems and methods for aquaponics and greenhouse technologies, and more particularly to systems and methods for solar greenhouse aquaponics and black soldier fly (BSF) composter and auto fish feeder, and the like.

Discussion of the Background

In recent years, aquaponics and greenhouse systems have been developed. However, such systems typically are lacking in effective incorporation of greenhouse and fish feeding systems for the aquaponics, in an efficient and cost-effective manner.

SUMMARY OF THE INVENTION

Therefore, there is a need for a method and system that addresses the above and other problems. The above and other problems are addressed by the illustrative embodiments of the present invention, which provide systems and methods for solar greenhouse aquaponics and black soldier fly (BSF) composter and auto fish feeder, and the like.

Accordingly, in illustrative aspects of the present invention there is provided a system, method and computer program product for an aquaponics, and greenhouse system, including a solar greenhouse insulated on north, east and west sides and with glazing on a south side at an angle to maximize winter sunlight, and housing a fish tank, grow beds, and a hard filter. The grow beds and hard filter include geyser pumps in the fish tank powered by air pumps that pump water from the fish tank to the grow bed or hard filter and aerate fish tank water. The hard filter includes algae layer with an air stone powered by an air pump underneath to aerate the algae. Grow beds on the north side have a barrier layer over media, and with a mushroom bulk substrate layer disposed thereover. The air intake of the air pump of the hard filter or the air stone extract $CO_2$ from the mushroom bulk substrate and pump the extracted $CO_2$ to the algae layer.

The system, method and computer program product can include a water wall configured as a thermal battery disposed on the north side of the greenhouse, wherein the one or more grow beds that are disposed on the north side of the greenhouse are located behind the water wall.

The system, method and computer program product can include a secondary roof plenum disposed underneath the roof of the greenhouse and coupled to a rain gutter water reservoir on a north side thereof. A water filter is coupled to the rain gutter water reservoir and configured to filter water from the rain gutter water reservoir. A water pump is coupled to the filter and configured to pump the filtered water to a mister spray head on an upper portion of the secondary roof plenum so that a water mist is sprayed and configured to condense within a channel formed by the roof of the greenhouse and the secondary roof plenum and return to the rain gutter water reservoir.

The hard filter includes mechanical filtration, biological filtration, chemical filtration, and/or UV light sanitation. A duckweed auto fish feeder is included and having an output coupled to the fish tank and with duckweed growing on a top water surface of the hard filter provided to the fish tank.

The system, method and computer program product can include a black soldier fly (BSF) composting and auto fish feeder for converting organic matter into BSF larvae for fish feed, and comprising a BSF container having an internal ramp, and an external ramp, with the internal ramp disposed within the BSF container, and with the external ramp coupled to the internal ramp and disposed over the fish tank so that the BSF larvae can crawl up the internal ramp and drop off from the external ramp into the fish tank as the fish feed.

The system, method and computer program product can include a spectral analyzer based sensor having a gas probe disposed within the greenhouse to measure air parameters of the greenhouse including temperature, humidity, $O_2$, and $CO_2$ levels in the greenhouse, and a water probe disposed within the fish tank to measure water parameters of the fish tank water including dissolved oxygen, PH, nitrate, nitrite, ammonia, and electrical conductivity (EC) levels of the fish tank water, and a computer coupled to the spectral analyzer based sensor and configured to control one or more of the air and water parameters based on the measured air and water parameters levels.

Each of the grow beds includes a bell siphon external to the grow bed and configured to drain the water from the grow bed back into the fish tank and from the grow bed back into the respective hydroponic tank. Each bell siphon comprises a bell siphon housing with an open end and closed top, with the open end of the bell siphon housing coupled to a bottom of the grow bed, and a bell siphon standpipe extending within the bell siphon housing and coupled to the fish tank to drain the water from the grow bed back into the fish tank, and to the respective hydroponic tank via respective valves.

Each of the fish tank and hard filter geyser pumps comprises a geyser pump housing with an open bottom and closed top, with an air inlet provided in the geyser pump housing coupled to the air pump, and a geyser pump standpipe extending through the closed top of the geyser pump housing to an inside of the geyser pump housing and coupled to a top of the grow bed to pump and aerate the water from the fish tank to the top of the grow bed.

Still other aspects, features, and advantages of the present invention are readily apparent from the following detailed description, by illustrating a number of illustrative embodiments and implementations, including the best mode contemplated for carrying out the present invention. The present invention is also capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The embodiments of the present invention are illustrated by way of example, and not by way of limitation, in the figures of the accompanying drawings and in which like reference numerals refer to similar elements and in which:

FIG. 1 is a top view diagram for illustrative systems and methods for solar greenhouse aquaponics and black soldier fly (BSF) composter and auto fish feeder, and the like;

FIG. 2 is an east view diagram for the illustrative systems and methods for solar greenhouse aquaponics and black soldier fly (BSF) composter and auto fish feeder, and the like;

FIGS. 3A-3D are diagrams for venting and door layouts for the illustrative systems and methods for solar greenhouse aquaponics and black soldier fly (BSF) composter and auto fish feeder, and the like;

FIG. 4 is diagram for a black soldier fly (BSF) composter and auto fish feeder for the illustrative systems and methods for solar greenhouse aquaponics and black soldier fly (BSF) composter and auto fish feeder, and the like;

FIG. 5 is diagram for a rocket mass heater (RMH) for the illustrative systems and methods for solar greenhouse aquaponics and black soldier fly (BSF) composter and auto fish feeder, and the like;

FIG. 6 is diagram for a geyser pump (GP) for the illustrative systems and methods for solar greenhouse aquaponics and black soldier fly (BSF) composter and auto fish feeder, and the like;

FIG. 7 is diagram for a bell siphon (BS) for the illustrative systems and methods for solar greenhouse aquaponics and black soldier fly (BSF) composter and auto fish feeder, and the like;

FIG. 8 is diagram for a rain water collection system (RWC) for the illustrative systems and methods for solar greenhouse aquaponics and black soldier fly (BSF) composter and auto fish feeder, and the like;

FIGS. 9A-9B are diagrams for an auto vent opener system for the illustrative systems and methods for solar greenhouse aquaponics and black soldier fly (BSF) composter and auto fish feeder, and the like;

FIGS. 10-11 are diagrams for water collection and processing systems for the illustrative systems and methods for solar greenhouse aquaponics and black soldier fly (BSF) composter and auto fish feeder, and the like;

FIG. 12 is a diagram for a multi-level system version of the illustrative systems and methods for solar greenhouse aquaponics and black soldier fly (BSF) composter and auto fish feeder, and the like;

FIG. 13 is a diagram for additional features for the illustrative systems and methods for solar greenhouse aquaponics and black soldier fly (BSF) composter and auto fish feeder, and the like;

FIGS. 14A-14B is an illustrative hard filter employed in the systems and methods for solar greenhouse aquaponics and black soldier fly (BSF) composter and auto fish feeder of FIGS. 1-13;

FIG. 15 is an illustrative geyser pump air distribution configuration employed in the systems and methods for solar greenhouse aquaponics and black soldier fly (BSF) composter and auto fish feeder of FIGS. 1-14 and 16-17;

FIG. 16 is an illustrative rocket mass heater configuration employed in the systems and methods for solar greenhouse aquaponics and black soldier fly (BSF) composter and auto fish feeder of FIGS. 1-15 and 17;

FIG. 17 is an illustrative on-demand aquaponics or hydroponics configuration employed in the systems and methods for solar greenhouse aquaponics and black soldier fly (BSF) composter and auto fish feeder of FIGS. 1-16;

FIGS. 20A-20B are illustrative mushrooms and greens fruiting chamber configurations employed in the systems and methods for solar greenhouse aquaponics and black soldier fly (BSF) composter and auto fish feeder of FIGS. 1-19 and 21; and FIG. 21 is an illustrative solar greenhouse with a natural air ventilation configuration employed in the systems and methods for solar greenhouse aquaponics and black soldier fly (BSF) composter and auto fish feeder of FIGS. 1-20.

DETAILED DESCRIPTION OF THE PREFERRED EMBODIMENTS

Figure 1:
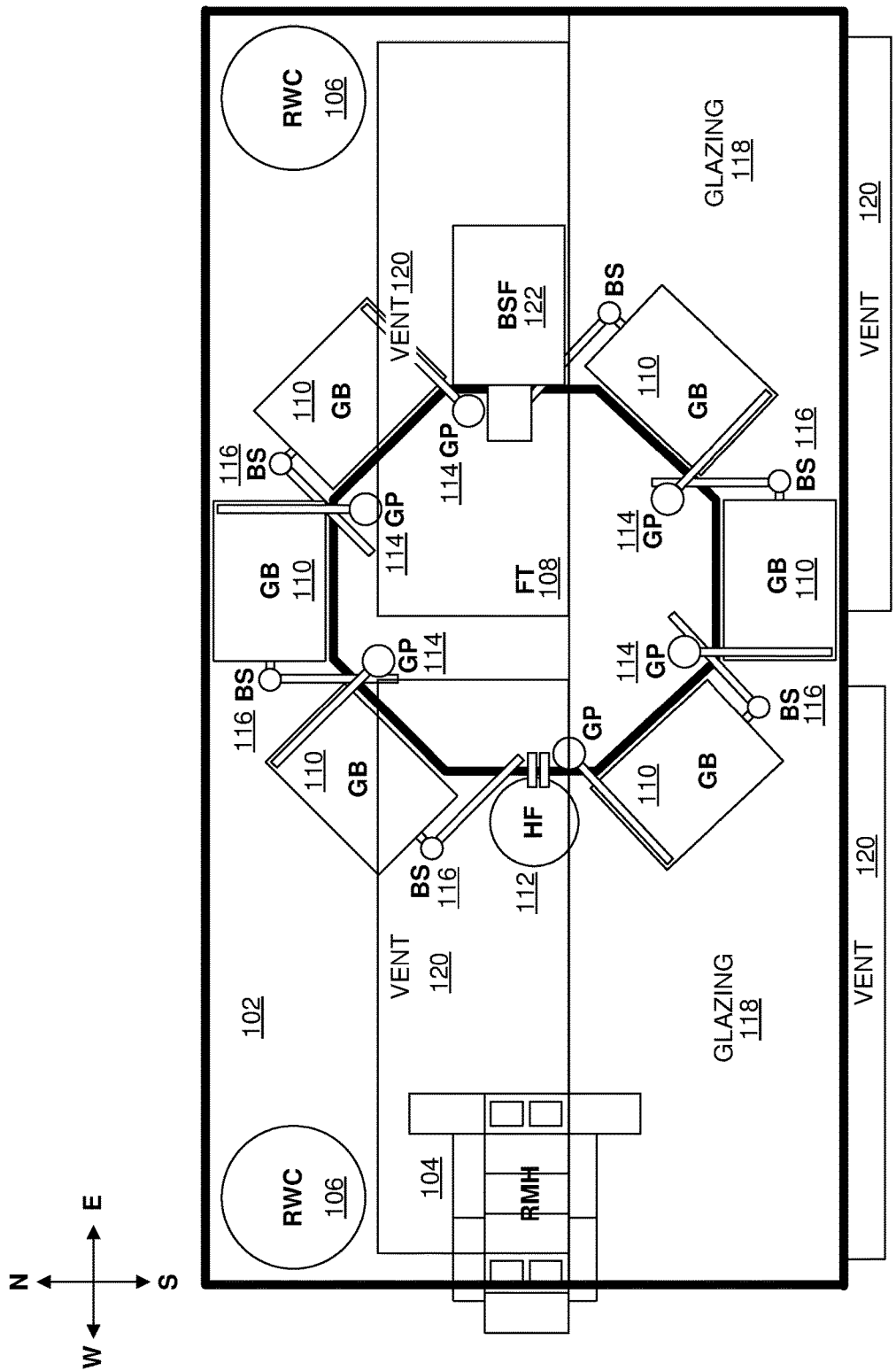

Referring now to the drawings, wherein like reference numerals designate identical or corresponding parts throughout the several views, and more particularly to FIG. 1 thereof, there shown a top view diagram 100 used for illustrative systems and methods for solar greenhouse aquaponics and black soldier fly (BSF) composter and auto fish feeder systems, and the like.

In FIG. 1, the system can include a solar greenhouse 102 (e.g., based on a Chinese solar greenhouse design, etc.) having a rocket mass heater 104 (RMH, e.g., made from fireplace bricks, metal vents, etc.) for additional heating the greenhouse and fish tank water, as needed, a rain water collection system 106 (RWC) for collecting rain water and heating the fish tank water, as needed, a fish tank 108 (FT, e.g., circular or octagonal shaped of 300-400 gallon capacity, cone bottom, etc.) for stocking fish (e.g., Tilapia, catfish, blue gills, perch, etc.), six or more grow beds 110 (GB, e.g., 27-30 gallon containers, media, deep water culture, wicking, etc.) arranged around the fish tank 108, and a hard filter 112 (HT, e.g., including mechanical, biological, chemical filtration, UV light sanitation, etc.) for additional filtering of the fish tank water, as needed. Each grow beds 110 is filled with media (e.g., expanded clay, pea gravel, soil, water, etc.) and can be fitted with respective air pump (not shown) connected to a geyser pump 114 (GP) for pumping and aerating the fish tank water from the fish tank 108 into the grow bed 110, and a bell siphon 116 for draining the water from the grow bed 110 to the fish tank 108. The greenhouse 100 can be dug into to the ground (not shown) with the east, west and north sides insulated by the earth and with the south side including a glazing 118 (e.g., 8'×4' triple wall polycarbonate panels, greenhouse plastic sheeting, glass, etc.) at an angle to maximize winter sunlight (e.g., as in an earth-sheltered design, etc.). Otherwise, the east, west and north sides can be insulated using insulation boards (not shown, e.g., 2 inch Rmax Thermashield 3 insulation, etc.), and the like. Vents 120 (e.g., including solar panels, wind turbines, etc., (not shown) to provide solar power, etc.) can be sized based on the greenhouse volume and provided on the lower east and south walls, on the upper north roof, and on the upper west side for ventilation, as needed, and based on wind direction, and the like. The greenhouse 100 can include a black soldier fly (BSF) composter and auto fish feeder 122, and a duckweed auto fish feeder (not shown, e.g., with duckweed growing on the hard filter 112 having output to fish tank 108, etc.).

Figure 2:
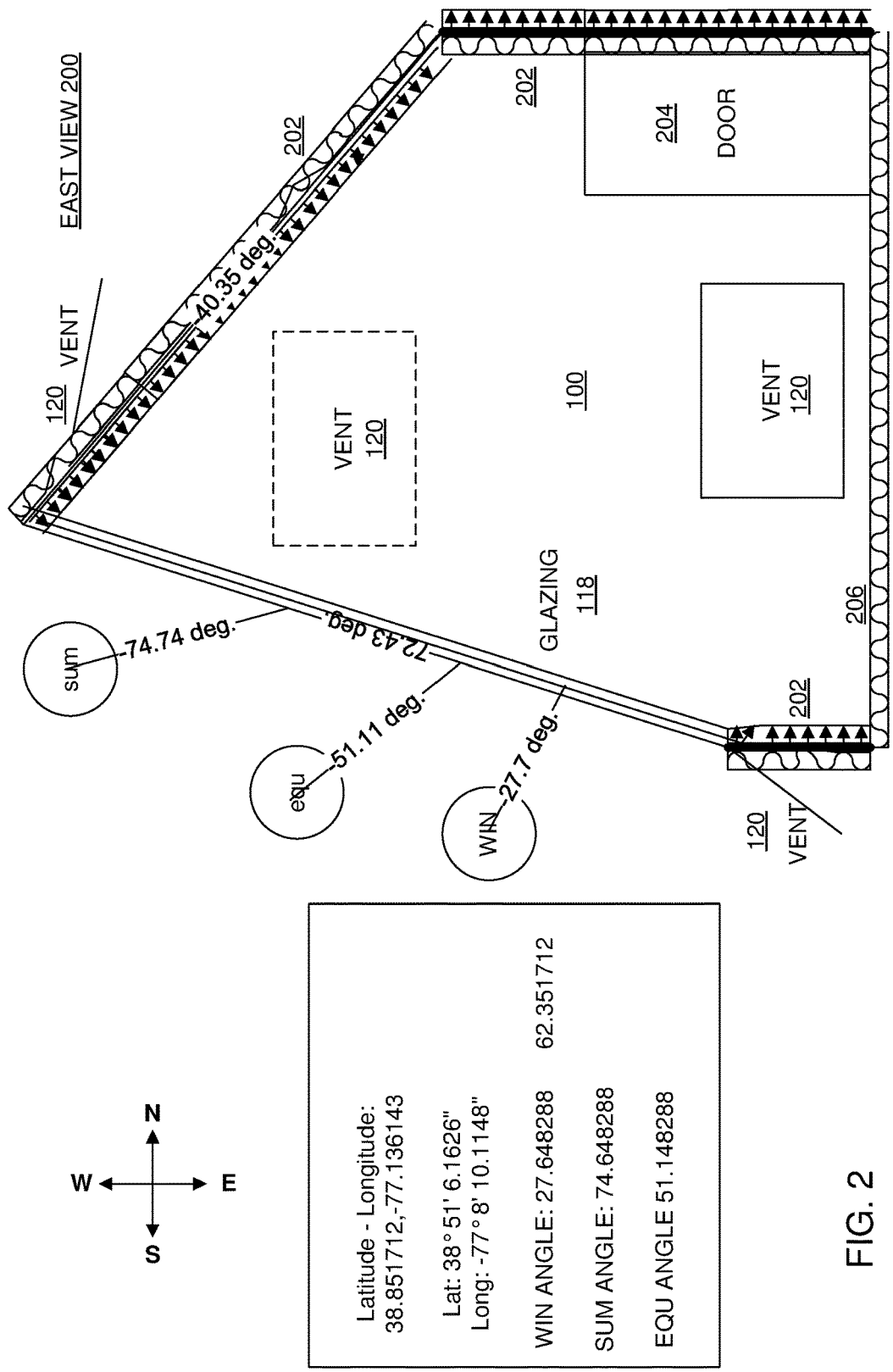

FIG. 2 is an east view diagram 200 for the illustrative systems and methods for solar greenhouse aquaponics and black soldier fly (BSF) composter and auto fish feeder, and the like. In FIG. 2, the glazing 118 (e.g., 8'×4' triple wall polycarbonate panels, greenhouse plastic sheeting, glass, etc.) is provided on the south facing wall at an angle to maximize winter (or e.g., summer, spring, fall, etc.) sunlight. The east, west and north sides can be insulated using insulation boards 202 (e.g., 2 inch Rmax Thermasheath 3 insulation, etc.), and the like. The insulation boards 202 can be reflective on the inside and/or outside, as needed, to reflect and/or trap heat within the greenhouse (e.g., based on the greenhouse effect, etc.). A solar blanket (not shown, e.g., automatically controlled, etc.) can be provide to insulate the glazing 118 at night or during dark periods, and the like, as needed. The vents 120 can be sized based on the greenhouse volume and provided on the lower east and south walls, on the upper north roof, and on the upper west side for ventilation, as needed, and based on wind direction, and the like. Doors 204 can be provided as needed, and the greenhouse 100 can be built on top of an insulated layer 206 (e.g., made from wood or plastic pallets, plastic shelves, concrete, etc.). The vents 120 can employ electronics motors and/or auto greenhouse solar window openers (e.g., wax filled cylinders/pistons that open upon heating, etc.) that are programmable to fully open within a suitable temperature range (e.g., a 40-80 degree Fahrenheit, etc.).

FIGS. 3A-3D are diagrams for venting and door layouts for the illustrative systems and methods for solar greenhouse aquaponics and black soldier fly (BSF) composter and auto fish feeder, and the like. In FIGS. 3A-3D, venting 120 and door layouts 204 are shown for (A) east side, (B) west side, (C) south side, and (D) top view. The vents 120 on the lower south side are programmable, as described above, and feed the vents 120 on the upper north side to create natural ventilation within the greenhouse.

FIG. 4 is diagram for a black soldier fly (BSF) composter and auto fish feeder 122 for the illustrative systems and methods for solar greenhouse aquaponics and black soldier fly (BSF) composter and auto fish feeder, and the like. In FIG. 4, the BSF composter and auto fish feeder 122 includes a housing 402 (e.g., made from a 30 gallon black plastic tote, etc.). The housing 402 is filled with media 404 (e.g., reptile bedding material, coco coir, etc.) that holds BSF larvae 406. Organic matter 408 is placed on top of the media through a lid 410 for the BSF larvae 406 to consume. When the larvae 406 are ready to become flies, they crawl up an inner ramp 412 (e.g., at 30-45 degrees, etc.) to an outer ramp 414 and drop into the fish tank 108 (not shown) to be consumed by the fish. Advantageously, the BSF system 122 acts as a highly efficient composter for most organic matter, and the larvae 406 provide for a high quality fish feed. An entrance hole 416 is provided for pregnant black soldier flies to enter and lay their eggs, thus generating more BSF larvae 406. An outlet 418 is provided to capture leachate juices 420 from the BSF composter and which can be diluted with water (e.g., at 20:1, etc.) and put back in the fish tank 108 (not shown) to be provided to the grow beds 110 (not shown) as fertilizer.

FIG. 5 is diagram for a rocket mass heater (RMH) 104 for the illustrative systems and methods for solar greenhouse aquaponics and black soldier fly (BSF) composter and auto fish feeder, and the like. In FIG. 5, the rocket mass heater 104 includes an L-shaped mass chamber 502 with burning wood and air 504 entering at one end, and with heated air 506 exiting at the other end to heat the greenhouse 100 (not shown). The RMH 104 can include a large mass (e.g., fire place bricks, etc.) that is heated and retains heat to be dissipated throughout the greenhouse 100 (not shown). Metal coils 508 can be wrapped around the RMH 104 to heat the fish tank water, as needed, with some electronically controlled valves 510, and the like (e.g., for computer, internet control, etc.). The RMH 104 can be buried within the floor of the greenhouse 100 (not shown) with a layer of gravel over the top to minimize the footprint.

FIG. 6 is diagram for a geyser pump (GP) 114 for the illustrative systems and methods for solar greenhouse aquaponics and black soldier fly (BSF) composter and auto fish feeder, and the like. In FIG. 6, the geyser pump 114 can include a large air chamber 602 (e.g., 4" white plastic PVC pipe, etc.) with a water stand pipe 604 (e.g., 1" white plastic PVC pipe, etc.) fitted in a center thereof. An air pump 606 (e.g., an 18-35 watt air pump running from electric, solar, wind power, etc.) is connected to an air line 608 (e.g., ¼" plastic line, etc.) that pumps air into the bottom of the air chamber 602. As the air chamber 602 fills with air, water from the bottom of the air chamber 602 is pumped to the grow bed 110 (not shown), while the fish tank 108 (not shown) water is aerated. Advantageously, each grow bed 110 (not shown) includes its own geyser pump 114 and air pump 606 providing for low energy requirements, water pumping, aeration, redundancy, and the like.

FIG. 7 is diagram for a bell siphon (BS) 116 for the illustrative systems and methods for solar greenhouse aquaponics and black soldier fly (BSF) composter and auto fish feeder, and the like. In FIG. 7, the bell siphon 116 can include a bell pipe 702 (e.g., 2"-4" white plastic PVC pipe, etc.), a stand pipe 704 (e.g., ½"-1" white plastic PVC pipe, etc.), and a siphon break line 706 (e.g., ¼"-½" clear or opaque plastic tubing, etc.). A water pipe 708 inside the grow bed 110 and connected to the bell pipe 702 takes in water from the grow bed 110. When the water reaches a siphon level 710 set by the stand pipe 704 lower than a media level 712 (e.g., approximately 2" above siphon level 710, etc.), the water starts a siphon effect and drains the water from the grow bed 110 into the fish tank 108 (not shown) faster than the water can be pumped in by the geyser pump 114 (not shown). When the water level goes down to the bottom of the siphon break 706, air is drawn in breaking the siphon, and starting a flooding cycle in the grow bed 110 from water pumped in by the geyser pump 114. Advantageously, the bell siphon 116 is located external to the grow bed 110 for ease of cleaning, maintenance, and the like.

FIG. 8 is diagram for a rain water collection system (RWC) 108 for the illustrative systems and methods for solar greenhouse aquaponics and black soldier fly (BSF) composter and auto fish feeder, and the like. In FIG. 8, the RWC system 108 can include the outside edges of the roof of the greenhouse 100 fitted with reflective gutters 802 for capturing rain. The captured rain flows through a rain water capture line 804 into one or more water collection tanks 806 (e.g., black 55 gallon, plastic drums, water wall, etc.) inside the greenhouse 100. The first water collection tank 806 can include lime stone 808, and the like, at a bottom thereof for adjusting the PH and can overflow via a connection line 810 into further water collection tanks 806. The last water collection tank 806 can include a water pump 812 (or e.g., can operate based on gravity, etc.) for pumping water into the fish tank 108 (not shown), as needed (e.g., based on a float arrangement, electronic sensor, etc.). Water from the fish tank 108 can be pumped or gravity fed to a fish tank heating line 814 for circulation in the reflective gutter 802 for solar heating of the fish tank water via electronically controlled valves 812, and the like (e.g., for computer, internet control, etc.). Advantageously, with the RWC system 106, rain water can be collected for use by the fish tank 108, fish tank water can be heated, additional water mass for solar heating by the greenhouse 100 can be provided, and the like.

FIGS. 9A-9B are diagrams for auto vent opener system 900 for the illustrative systems and methods for solar greenhouse aquaponics and black soldier fly (BSF) composter and auto fish feeder, and the like. In FIG. 9, the auto vent opener system 900 can include vents (A) on the north roof, and (B) on the lower south wall of the greenhouse 100, employing electronics motors (not shown) and/or auto greenhouse solar window openers 902 (e.g., wax filled cylinders/pistons that open upon heating, etc.) that are programmable to fully open within a suitable temperature range (e.g., a 40-80 degree Fahrenheit, etc.).

The illustrative embodiments of FIGS. 1-9 can be fitted with additional computer controlled sensors (e.g., temperature, humidity, O2, CO2, H2O, dissolved oxygen, PH, nitrate, nitrite, ammonia, electrical conductivity (EC), etc.) for greenhouse and aquaponics automation over a LAN or the Internet, and the like, as further described.

FIGS. 10-11 are diagrams for water collection and processing systems 1000-1100 for the illustrative systems and methods for solar greenhouse aquaponics and black soldier fly (BSF) composter and auto fish feeder, and the like. In FIG. 10, the water collection and processing systems 1000 can include a black colored water wall 1002 inside the greenhouse 100 for collecting rainwater and/or receiving rainwater from the RWC 106 and/or a cistern (not sown). A filter 1004 and purifier 1006 is included to provide clean water 1008 to the fish tank 108, the RWC 106, for human use, and the like. In FIG. 11, the water collection and processing systems 1000 can include collected rainwater 1102, cistern water 1104, and gray water 1106 fed to the filter 1004 and purifier 1006 to provide clean water 1008 for human use 1108 that feeds the gray water 1106. The clean water 1008 also feeds the fish tank 108 that then feeds the hard filter 112 that feeds the grow beds 110 that feeds water back to the fish tank 108 completing the loop. The fish tank 108 and the grow beds 110 can also be decoupled with respective hard filters, as needed, to optimize for fish and/or plant growth.

FIG. 12 is a diagram for a multi-level system version 1200 of the illustrative systems and methods for solar greenhouse aquaponics and black soldier fly (BSF) composter and auto fish feeder, and the like. In FIG. 12, the multi-level system version 1200 can be sheltered in the ground 1202 and/or insulated as previously described, and with geothermal heating and/or venting 1204. Each level 1206 separated by grated floors 1208 can include the grow beds 110 fed from the fish tank 108 via the hard filter 106 and with respective vents/solar panels 120 on the south side and north roof having RWC 106. A sensor/CPU system 1210 (e.g., spectral analyzer based, etc.) with gas 1212 and liquid 1214 probes can be used to measure and control all relevant air and water parameters (e.g., temperature, humidity, O2, CO2, H2O, dissolved oxygen, PH, nitrate, nitrite, ammonia, electrical conductivity (EC), etc.) of the fish tank 108 and grow beds 110 at every level 1206, as needed, including internet monitoring and control via suitable software applications, and the like. A battery and inverter system 1216 can be provided for on and/or off grid operation and switching from the solar panels 120 and/or wind turbine (not shown), including powering additional lighting (not shown), and the like.

Figure 13:
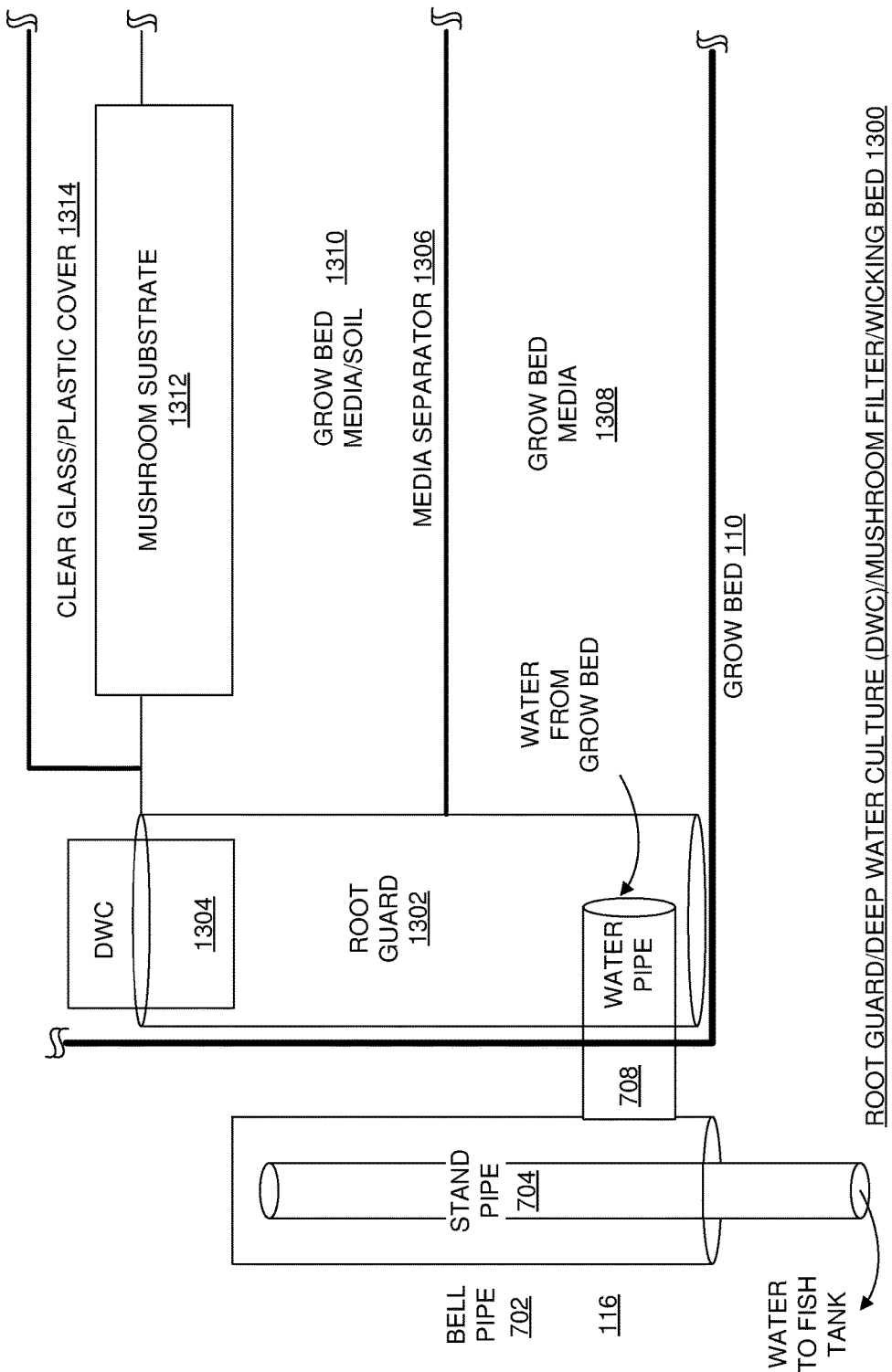

FIG. 13 is a diagram for additional features 1300 for the illustrative systems and methods for solar greenhouse aquaponics and black soldier fly (BSF) composter and auto fish feeder, and the like. In FIG. 13, the additional features 1300 can include a root guard 1302 for the bell siphon 116 for ease of cleaning and maintenance, and for providing deep water culture (DWC) functionality via a media filled net pot or a raft 1304 within the media bed grow bed 110. The grow bed 110 can also be configured a wicking bed by providing media separator 1306 (e.g., made of burlap or weed guard material, etc.) between hydroponic media 1308 and/or soil media 1310. A mushroom substrate 1312 with a clear glass or plastic cover 1314 can be placed in the media 1310 for growing edible mushrooms, advantageously, providing exchange of CO2 and O2, biological filtering of nitrates, an additional food source, and the like. The flood and drain action of the grow bed 110, advantageously, maintains humidity and provides air exchange, and the like, for mushroom cultivation, and the like.

FIGS. 14A-14B is an illustrative hard filter employed in the systems and methods for solar greenhouse aquaponics and black soldier fly (BSF) composter and auto fish feeder of FIGS. 1-13. In FIGS. 14A-14B, the hard filter 112 can include a water inlet pipe 1402. The water inlet pipe 1402 can be fed with water from the fish tank 108 via a geyser pump or water pump (not shown) coupled to the fish tank 108. The input water from the water inlet pipe 1402 is fed to a stilling well 1404 that couples to a funnel-shaped settling chamber 1406. The funnel-shaped settling chamber 1406 is coupled to a valve 1408 coupled to an output drain pipe 1410 for purging fish waste that is settled in the settling chamber 1406. The water input from the water inlet pipe 1402 fills up in the settling chamber 1406 and then rises and passes through a series of one or more media filters 1412 (e.g., Matala® type advanced filter media) configured around the stilling well 1404, and starting from the bottom of the settling chamber 1406 with a coarse filter 1412 up to a fine filter 1412 near the top of the stilling well 1404. The water then rises and is filtered through the media filters 1412. The filtered water then enters a weir chamber 1414 having air stones 1420 resting on the top media filter 1412. The air stones 1420 provide for degassing of the filtered water in the weir chamber 1414. Around the weir chamber 1414 is provided a sponge type filter 1416 to further filter the water before the filtered water is output through an output pipe 1418 back to the fish tank 108 and/or grow beds 110. Water plants and algae (not shown), such as Duckweed, beneficial algae, and the like, can be grown in the filtered water in the weir chamber 1414 for further filtering of the water and for use as fish feed supplements. Advantageously, the algae grown in the weir chamber 1414 can include omega fatty acids typically missing from conventional farmed fish. Employing a geyser pump (not shown) to feed the water inlet pipe 1402, advantageously, allows for the system of FIGS. 1-14 to be run without employing any conventional water pumps, as with conventional aquaponics systems.

FIG. 15 is an illustrative geyser pump air distribution configuration employed in the systems and methods for solar greenhouse aquaponics and black soldier fly (BSF) composter and auto fish feeder of FIGS. 1-14 and 16-17. In FIG. 15, the geyser pump 114 air distribution configuration can include respective solar panels 1502 (and/or e.g., small wind turbines, not shown) and batteries 1504 coupled to the respective air pumps 606 for the respective grow beds 110 (not shown). The air pumps 106 are coupled to respective air tanks 1506 via one way valves 1508. The respective air tanks 1506 are coupled in series via respective pressure release valves 1510 configured for maintaining a suitable air pressure to power the respective geyser pumps 114. As the first air tank fills to pressure, the valves 1510 allow for filling of the subsequent air tanks 1506 until the last tank 1506 is full. When the air tanks 1506 are filled to capacity, the power to the air pumps 606 from the batteries 1504 can be turned off with a suitable air powered solenoid switch (not shown) and triggered by one or more of the respective pressure release valves 1510. Advantageously, such air distribution configuration allows for the system to be run solely from air and via solar power and/or wind power, and with N-way redundancy.

FIG. 16 is an illustrative rocket mass heater configuration employed in the systems and methods for solar greenhouse aquaponics and black soldier fly (BSF) composter and auto fish feeder of FIGS. 1-15 and 17. In FIG. 16, the rocket mass heater 104 configuration can include a rocket stove 1602 having an air feed 1608, fuel chamber 1606 and heated gas output 1610. The heated gas output 1610 is coupled to one or more suitable masses 1604 (e.g., cylindrical or square tube shaped clay flue pipes, etc.) coupled to each other via respective gas input and exhaust ports 1612 and 1614. The exhaust port of the final mass 1604 can be coupled to a gas exit pipe (not shown). Advantageously, the hot gasses from the gas output 1610 of the rocket stove 1602 enter the first mass 1604 and rise, and then exit when cooled down from a lower portion thereof via the first gas output 1612 coupled to the second mass 1604, and so on, to efficiently heat each of the masses 1604 with cooler and cooler gasses in series.

FIG. 17 is an illustrative on-demand aquaponics or hydroponics configuration employed in the systems and methods for solar greenhouse aquaponics and black soldier fly (BSF) composter and auto fish feeder of FIGS. 1-16. In FIG. 17, the on-demand aquaponics or hydroponics configuration 1700 can include respective hydroponics tanks 1702 having respective geyser pumps 1704 therein for pumping hydroponic water from the tanks 1702 to the respective grow beds 110 that can also be fed with water from the fish tank 108 via the respective geyser pumps 114. Respective air switches 1706 allow for selection of air to be delivered to the respective geyser pumps 1704 and/or 114. The respective output water from the grow beds 110 can be cycled back to the respective hydroponics tanks 1702 and/or the fish tank 108 via respective selector valves 1708 and 1710. Advantageously, each of the grow beds 110 can be configured to cycle water from the fish tank 108 and/or the respective hydroponics tanks 1702. Such a configuration, advantageously, allows for cycling of, for example, high nitrate fish tank 108 water to one or more of the grow beds 110 for vegetative growth by sending air to only one or more of the geyser pumps 114 via suitable configuration of the respective air switches 1706 and the respective selector valves 1708 and 1710. After a desired vegetative growth stage is complete in one or more of the grow beds 110, cycling of, for example, low nitrate, high phosphorous and potassium, and the like, hydroponics tanks 1702 water to one or more of the grow beds 110 for flower and fruiting growth can be accomplished by sending air to only one or more of the geyser pumps 1704 via suitable configuration of the respective air switches 1706 and the respective selector valves 1708 and 1710. Advantageously, plants that require high nitrates and/or plants that require low nitrates and high phosphorous and potassium, and the like, can be accommodated in one or more of the respective grow beds 110 with suitable configuration of the respective air switches 1706 and the respective selector valves 1708 and 1710.

Figure 18:
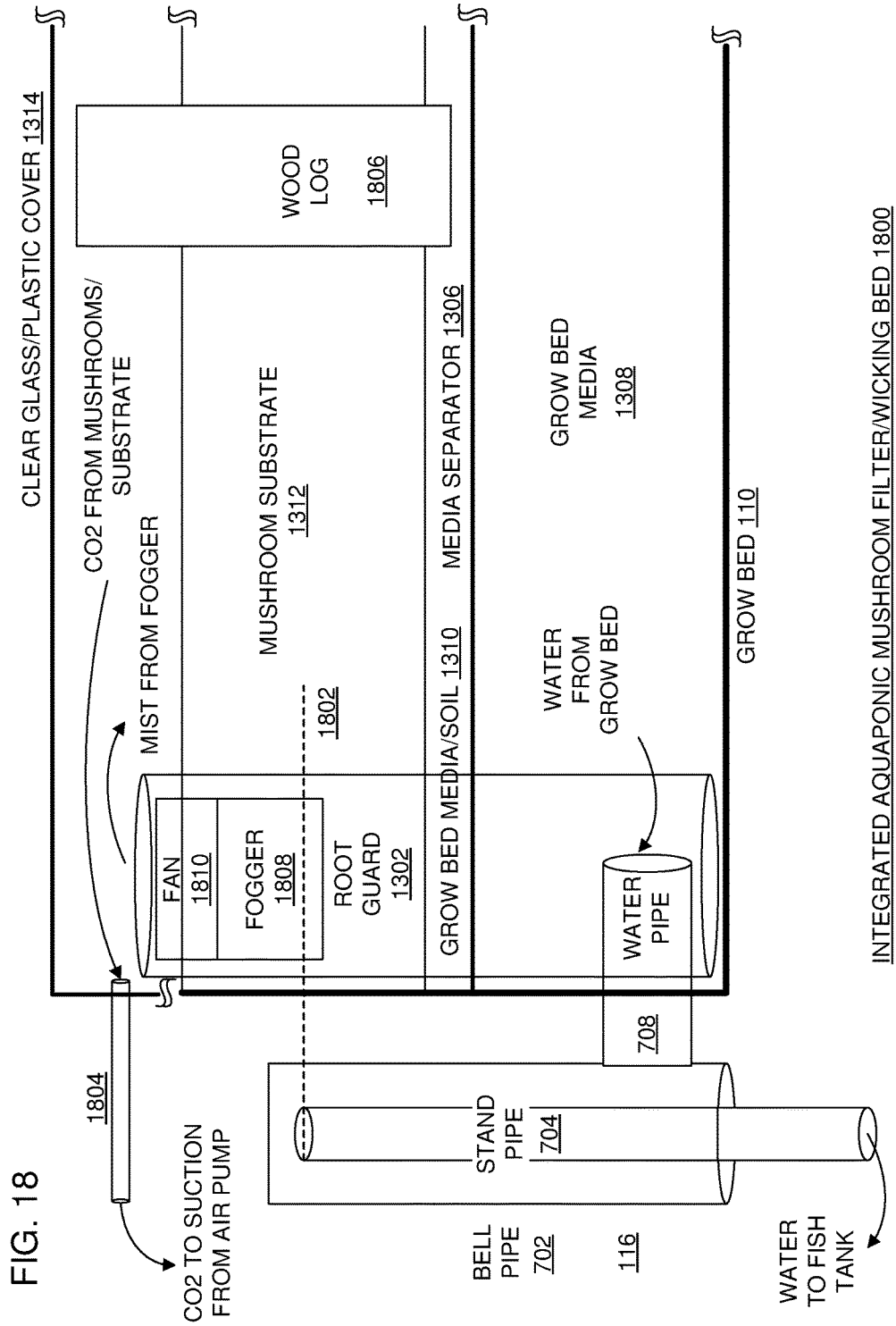
FIG. 18 is an illustrative aquaponic mushroom filter and wicking bed configuration employed in the systems and methods for solar greenhouse aquaponics and black soldier fly (BSF) composter and auto fish feeder of FIGS. 1-17 and 19-21.

FIG. 18 is an illustrative aquaponic mushroom filter and wicking bed configuration employed in the systems and methods for solar greenhouse aquaponics and black soldier fly (BSF) composter and auto fish feeder of FIGS. 1-17 and 19-21. In FIG. 18, the mushroom substrate 1312 is included over the media separator 1306, such that the bell siphon 116 floods and drains the mushroom substrate 1312 up to a water level 1802 determined by the standpipe 704. In this way, the mushroom substrate 1312 can be hydrated to increase fruiting, in addition to adding beneficial microbes, during flood and drain cycles, advantageously, increasing mushroom fruit production. Advantageously, the mushroom substrate 1312 can be inoculated and colonized directly in the flood and drain media grow bed 110. During the colonization stage, the flood and drain action is turned off, for example, by turning off the air supply to the geyser pump that feeds the grow bed 110, so that the mycelium can fully colonize the mushroom substrate 1312. After the mushroom substrate 1312 is fully colonized, the flood and drain mechanism can be turned back on, so is to hydrate the mushroom substrate 1312 for increased fruiting, as previously described. In addition, the water from the fish tank can include around 1-2 parts per thousand of salt for the fish health, and which also acts as an antibacterial agent to reduce contamination of the mushroom substrate 1312.

Advantageously, since the system can be fully air powered, the suction from the air pumps used to power the geyser pumps can be used to extract $CO_2$ from the mushroom substrate 1312 and mushroom fruits, thereby increasing fresh air exchange, and producing mushroom fruits with desirable characteristics. In addition, the $CO_2$ that is extracted from the mushroom substrate 1312 and mushroom fruits can be used by the algae and duckweed biofilter, previously described, for example, with respect to FIG. 14B, to create a closed loop system where the $CO_2$ from the mushrooms is employed by the algae and duckweed biofilter of FIG. 14B.

In further embodiments, a wood log or block 1806 that is inoculated with dowels colonized with mushroom mycelium can be inserted inside of the media of the grow bed 110 to create a natural log type mushroom cultivation system. Advantageously, plants can also be grown within the grow bed 110 for providing oxygen and carbon dioxide exchange between the plants and the mushroom logs 1806 and/or mushroom substrate 1312, and the mushrooms growing thereon.

In further embodiments, a fogger 1808 (e.g., of the ultrasonic type, etc.) with a fan 1810 can be positioned within the root guard 1302, such that when the root guard 1302 fills with water during flood and drain cycles, fog is created that is then distributed via the fan 1810 to the mushroom substrate 1312 or the logs 1803 and the mushrooms growing thereon, advantageously, increasing fresh air exchange.

Figure 19:
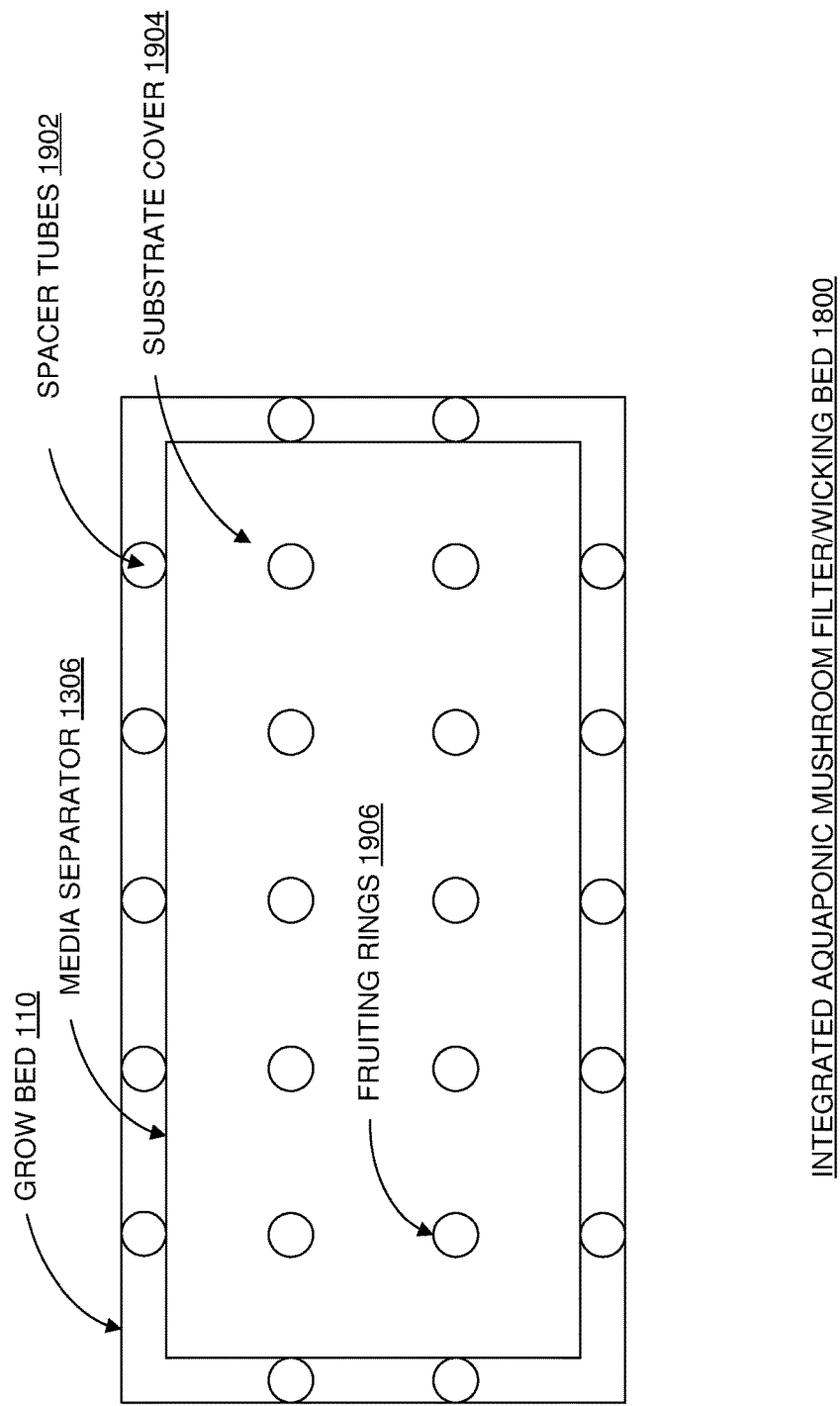
FIG. 19 is an illustrative aquaponic mushroom filter and wicking bed configuration employed in the systems and methods for solar greenhouse aquaponics and black soldier fly (BSF) composter and auto fish feeder of FIGS. 1-18 and 20-21.

FIG. 19 is an illustrative aquaponic mushroom filter and wicking bed configuration employed in the systems and methods for solar greenhouse aquaponics and black soldier fly (BSF) composter and auto fish feeder of FIGS. 1-18 and 20-21. In FIG. 19, spacer tubes 1902 are positioned between the media separator 1306 and the grow bed walls so is to create spaces around the mushroom substrate in the flood and drain media grow bed 110. Advantageously, this can increase the amount of air that is drawn around the mushroom substrate during the flood and drain action.

In addition, a substrate cover 1904, for example, made for a plastic material that does not transmit light can be sealed over top of the substrate, so as to maintain moisture in the substrate during the fruiting stages. Fruiting rings 1906 can be disposed within the substrate cover 1904 to provide points for mushroom fruiting dispersed along the entire substrate. Advantageously, the sizes of the mushroom flushes can be adjusted based on the number of fruiting rings 1906 employed within the substrate cover 1904. The fruiting rings 1906 can be positioned within the substrate cover 1904, and covered with a suitable filter material, for example, micropore type tape, polyfill, and the like, to reduce contamination, while allowing for fresh air exchange.

FIGS. 20A-20B are illustrative mushrooms and greens fruiting chamber configurations employed in the systems and methods for solar greenhouse aquaponics and black soldier fly (BSF) composter and auto fish feeder of FIGS. 1-19 and 21. In FIGS. 20A-20B, an insulated housing enclosure 2002 is provided with a shelving unit 2004, for example, of the type of shelving units used in restaurants, and the like. The shelving unit 2004 can include racks 2006 that can be configured for growing microgreens, edible plants, and the like.

The microgreens racks 2006 can be positioned in a lower portion of the shelving unit 2004, with mushroom logs or bags 2008 suspended in an upper portion of the shelving unit 2004. Advantageously, the CO2 produced by the mushroom logs and/or bags 2008 and/or mushrooms growing thereon, settles to the bottom of the shelving unit 2004 and is employed by the plants in the greens racks 2006. Similarly, the plant racks 2006 provide oxygen to the mushroom logs or bags 2008. Advantageously, air exchange and humidity can be maintained with such configuration so that humidifiers, fans, and the like, need not be employed.

Lights 2010 (e.g., LED type lights, grow lights, etc.) and the like, can be disposed within the housing 2002 and or the shelving unit 2004 to provide light for the plants in the greens rack 2006 and for the mushrooms growing on the logs or bags 2008. In further embodiments, and aquaponics type fish tank 2012 with a water or geyser type pump 2014 can be used to distribute nutrient rich water from the fish tank 2012 to the greens racks 2006 via the outlet 2018. A return line 2018 can return the filtered water from the greens racks 2006 back to the fish tank 2012. Advantageously, the humidity provided by the aquaponics component can be used to increase the humidity within the mushroom and greens fruiting chamber 2000, for improved plant and mushroom growth.

In FIG. 20B, the mushroom logs or bags 2008 can be placed on mushroom racks 2020, instead of or in addition to being hung from the shelving unit 2004, as shown in FIG. 20A. Advantageously, the racks 2006 and 2020, can be configured as conventional restaurant racks to allow for easy filling and removal of the mushrooms and plants, for example, in a restaurant type setting, and like. In further embodiments, fish tank 2012 need not be employed, wherein nutrient rich water from the fish tank 108 and/or one or more of the hydroponic tanks 1702 can be fed to the racks 2006 with the return 2018 coupled back to return the filtered water to the fish tank 108 and/or one or more of the hydroponic tanks 1702.

FIG. 21 is an illustrative solar greenhouse with a natural air ventilation configuration employed in the systems and methods for solar greenhouse aquaponics and black soldier fly (BSF) composter and auto fish feeder of FIGS. 1-20. In FIG. 21, a reservoir or gutter 2102 feeds water to a prefilter 2104 connected to a pump 2106 which supplies pressured water to a mister head 2110 via a water line 2108. The pressurized water from the pump 2106 provides a fine mist from the mister 2110 that is transmitted down to channel formed by a plenum or secondary roof 2112 that is underneath the north roof of the greenhouse. The channel 2114 that is formed, advantageously, produces a cold stream of air as the water that is misted condenses, thus, creating a natural air flow that flows down the channel to 2114 towards the bottom of the greenhouse.

Water that condenses from the mister 2110 is captured by the plenum 2112 and fed back to the gutter 2102 to be recycled and delivered back through the filter 2104 to the pump 2106 and the water line 2108 to the mister 2110. In further embodiments, a straw or similar material, and the like, type mat 2116 can be disposed in front of the mister 2110 with a fan 2118 drawing air through the mat 2116 to produce a swamp cooler, and the like, type effect within the channel 2114.

The cold air flowing through the channel 2114, can flow into a mushroom chamber 2120 with mushroom logs or bags 2008 dispose within the mushroom chamber 2120. Advantageously, the mushroom chamber 2120 can be located behind the water wall 1002 of the Chinese solar greenhouse. The cold air flowing down to channel 2114 into the mushroom chamber 2120, advantageously, can draw the carbon dioxide from the mushroom logs or bags 2008 towards the bottom of the greenhouse to be recycled by the plants on the other side of the water wall 1002. A fan 2122 can be provided, if needed, to further enhance the CO2 and O2 exchange from the mushroom chamber 2120 into the plant section of the greenhouse.

Advantageously, the cold air flowing through the channel 2114 and the mushroom chamber 2120, creates a natural circular circulation pattern, as the air cools and then is heated and rises and is expelled through the upper vent 120. The lower vent 120 also can introduce fresh cold air into the system and further helping the air circulate with the carbon dioxide in a circular pattern within the greenhouse. As with the previous embodiments, advantageously, CO2 and O2 gas exchange is provided to benefit both the plants and the mushrooms being cultivated. In further embodiments, one or more of the grow beds 110 configured for growing mushrooms, as previously described, can be located behind the water wall 1002 in the mushroom chamber 2120.

Advantageously, the illustrative systems and methods allow for efficient and cost-effective greenhouse, mushroom, and fish feeding systems for aquaponics, mushroom, and microgreens cultivation, and the like.

Although the illustrative systems and methods are described in terms of aquaponics, the illustrative systems and methods can be applied to any other types of aquaculture and greenhouse technologies, as will be appreciated by those of ordinary skill in the relevant arts.

The above-described devices and subsystems of the illustrative embodiments can include, for example, any suitable servers, workstations, PCs, laptop computers, PDAs, Internet appliances, handheld devices, cellular telephones, wireless devices, other devices, and the like, capable of performing the processes of the illustrative embodiments. The devices and subsystems of the illustrative embodiments can communicate with each other using any suitable protocol and can be implemented using one or more programmed computer systems or devices.

One or more interface mechanisms can be used with the illustrative embodiments, including, for example, Internet access, telecommunications in any suitable form (e.g., voice, modem, and the like), wireless communications media, and the like. For example, employed communications networks or links can include one or more wireless communications networks, cellular communications networks, G3 communications networks, Public Switched Telephone Network (PSTNs), Packet Data Networks (PDNs), the Internet, intranets, a combination thereof, and the like.

It is to be understood that the devices and subsystems of the illustrative embodiments are for illustrative purposes, as many variations of the specific hardware used to implement the illustrative embodiments are possible, as will be appreciated by those skilled in the relevant art(s). For example, the functionality of one or more of the devices and subsystems of the illustrative embodiments can be implemented via one or more programmed computer systems or devices.

To implement such variations as well as other variations, a single computer system can be programmed to perform the special purpose functions of one or more of the devices and subsystems of the illustrative embodiments. On the other hand, two or more programmed computer systems or devices can be substituted for any one of the devices and subsystems of the illustrative embodiments. Accordingly, principles and advantages of distributed processing, such as redundancy, replication, and the like, also can be implemented, as desired, to increase the robustness and performance of the devices and subsystems of the illustrative embodiments.

The devices and subsystems of the illustrative embodiments can store information relating to various processes described herein. This information can be stored in one or more memories, such as a hard disk, optical disk, magneto-optical disk, RAM, and the like, of the devices and subsystems of the illustrative embodiments. One or more databases of the devices and subsystems of the illustrative embodiments can store the information used to implement the illustrative embodiments of the present inventions. The databases can be organized using data structures (e.g., records, tables, arrays, fields, graphs, trees, lists, and the like) included in one or more memories or storage devices listed herein. The processes described with respect to the illustrative embodiments can include appropriate data structures for storing data collected and/or generated by the processes of the devices and subsystems of the illustrative embodiments in one or more databases thereof.

All ora portion of the devices and subsystems of the illustrative embodiments can be conveniently implemented using one or more general purpose computer systems, microprocessors, digital signal processors, micro-controllers, and the like, programmed according to the teachings of the illustrative embodiments of the present inventions, as will be appreciated by those skilled in the computer and software arts. Appropriate software can be readily prepared by programmers of ordinary skill based on the teachings of the illustrative embodiments, as will be appreciated by those skilled in the software art. Further, the devices and subsystems of the illustrative embodiments can be implemented on the World Wide Web. In addition, the devices and subsystems of the illustrative embodiments can be implemented by the preparation of application-specific integrated circuits or by interconnecting an appropriate network of conventional component circuits, as will be appreciated by those skilled in the electrical art(s). Thus, the illustrative embodiments are not limited to any specific combination of hardware circuitry and/or software.

Stored on any one or on a combination of computer readable media, the illustrative embodiments of the present inventions can include software for controlling the devices and subsystems of the illustrative embodiments, for driving the devices and subsystems of the illustrative embodiments, for enabling the devices and subsystems of the illustrative embodiments to interact with a human user, and the like. Such software can include, but is not limited to, device drivers, firmware, operating systems, development tools, applications software, and the like. Such computer readable media further can include the computer program product of an embodiment of the present inventions for performing all or a portion (if processing is distributed) of the processing performed in implementing the inventions. Computer code devices of the illustrative embodiments of the present inventions can include any suitable interpretable or executable code mechanism, including but not limited to scripts, interpretable programs, dynamic link libraries (DLLs), Java classes and applets, complete executable programs, Common Object Request Broker Architecture (CORBA) objects, and the like. Moreover, parts of the processing of the illustrative embodiments of the present inventions can be distributed for better performance, reliability, cost, and the like.

As stated above, the devices and subsystems of the illustrative embodiments can include computer readable medium or memories for holding instructions programmed according to the teachings of the present inventions and for holding data structures, tables, records, and/or other data described herein. Computer readable medium can include any suitable medium that participates in providing instructions to a processor for execution. Such a medium can take many forms, including but not limited to, non-volatile media, volatile media, transmission media, and the like. Non-volatile media can include, for example, optical or magnetic disks, magneto-optical disks, and the like. Volatile media can include dynamic memories, and the like. Transmission media can include coaxial cables, copper wire, fiber optics, and the like. Transmission media also can take the form of acoustic, optical, electromagnetic waves, and the like, such as those generated during radio frequency (RF) communications, infrared (IR) data communications, and the like. Common forms of computer-readable media can include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present inventions have been described in connection with a number of illustrative embodiments, and implementations, the present inventions are not so limited, but rather cover various modifications, and equivalent arrangements, which fall within the purview of the appended claims.

What is claimed is:

1. An aquaponics, and greenhouse system comprising:
a solar greenhouse insulated on north, east and west sides and with glazing on a south side at an angle to maximize winter sunlight, and housing:
a fish tank housed within the solar greenhouse;
a plurality of grow beds coupled to the fish tank and also housed within the solar greenhouse, wherein each one of the plurality of grow beds is coupled to a respective fish tank geyser pump internal to the fish tank, and
the fish tank geyser pumps are powered by an external air pump to pump water from the fish tank to the grow bed and aerate water of the fish tank; and
a hard filter coupled to the fish tank and having a hard filter geyser pump internal to the fish tank and powered by an external air pump to pump water from the fish tank to the hard filter to aerate and filter water of the fish tank, wherein the hard filter includes algae layer on an upper portion thereof with an air stone powered by an external air pump underneath the algae layer to aerate the algae,
one or more of the grow beds are disposed on the north side of the greenhouse and are configured with a barrier layer over media, and with a mushroom bulk substrate layer disposed over the barrier layer, and
one or more of an air intake of the external air pump of the hard filter geyser pump, and an air intake of the external air pump of the air stone is coupled to a top surface of the mushroom bulk substrate layer to extract $CO_2$ from the mushroom bulk substrate and pump the extracted $CO_2$ to the algae layer via one or more of the hard filter geyser pump, and the air stone.

2. The system of claim 1, further comprising:
a water wall configured as a thermal battery disposed on the north side of the greenhouse, wherein the one or more grow beds that are disposed on the north side of the greenhouse are located behind the water wall.

3. The system of claim 1, further comprising:
a secondary roof plenum disposed underneath the roof of the greenhouse and coupled to a rain gutter water reservoir on a north side thereof;
a water filter coupled to the rain gutter water reservoir and configured to filter water from the rain gutter water reservoir; and
a water pump coupled to the filter and configured to pump the filtered water to a mister spray head on an upper portion of the secondary roof plenum so that a water mist is sprayed and configured to condense within a channel formed by the roof of the greenhouse and the secondary roof plenum and return to the rain gutter water reservoir.

4. The system of claim 1, wherein the hard filter comprises:
mechanical filtration, biological filtration, chemical filtration, and/or UV light sanitation; and
a duckweed auto fish feeder having an output coupled to the fish tank and with duckweed growing on a top water surface of the hard filter provided to the fish tank.

5. The system of claim 1, further comprising:
a black soldier fly (BSF) composting and auto fish feeder for converting organic matter into BSF larvae for fish feed, and comprising a BSF container having an internal ramp, and an external ramp, with the internal ramp disposed within the BSF container, and with the external ramp coupled to the internal ramp and disposed over the fish tank so that the BSF larvae can crawl up the internal ramp and drop off from the external ramp into the fish tank as the fish feed.

6. The system of claim 1, further comprising:
a spectral analyzer based sensor having a gas probe disposed within the greenhouse to measure air parameters of the greenhouse including temperature, humidity, $O_2$, and $CO_2$ levels in the greenhouse, and a water probe disposed within the fish tank to measure water parameters of the fish tank water including dissolved oxygen, PH, nitrate, nitrite, ammonia, and electrical conductivity (EC) levels of the fish tank water, and
a computer coupled to the spectral analyzer based sensor and configured to control one or more of the air and water parameters based on the measured air and water parameters levels.

7. The system of claim 1, wherein each of the grow beds includes a bell siphon external to the grow bed and configured to drain the water from the grow bed back into the fish tank and from the grow bed back into the respective hydroponic tank, and
each bell siphon comprises a bell siphon housing with an open end and closed top, with the open end of the bell siphon housing coupled to a bottom of the grow bed, and a bell siphon standpipe extending within the bell siphon housing and coupled to the fish tank to drain the water from the grow bed back into the fish tank, and to the respective hydroponic tank via respective valves.

8. The system of claim 1, wherein each of the fish tank and hard filter geyser pumps comprises a geyser pump housing with an open bottom and closed top, with an air inlet provided in the geyser pump housing coupled to the air pump, and a geyser pump standpipe extending through the closed top of the geyser pump housing to an inside of the geyser pump housing and coupled to a top of the grow bed to pump and aerate the water from the fish tank to the top of the grow bed.

* * * * *